(12) United States Patent
Piomelli et al.

(10) Patent No.: US 9,187,413 B2
(45) Date of Patent: Nov. 17, 2015

(54) PERIPHERALLY RESTRICTED FAAH INHIBITORS

(75) Inventors: Daniele Piomelli, Irvine, CA (US); Jason R. Clapper, Irvine, CA (US); Guillermo Moreno-Sanz, Irvine, CA (US); Andrea Duranti, Urbino (IT); Andrea Tontini, Pesaro (IT); Giovanna Guiducci, legal representative, Pesaro (IT); Marco Mor, Ghedi (IT); Giorgio Tarzia, Petriano (IT)

(73) Assignees: The Regents of the University of California, Oakland, CA (US); Universita Degli Studi Di Parma, Parma (IT); Universita Degli Studi Di Urbino, Urbino (IT)

(*) Notice: Subject to any disclaimer, the term of this patent is extended or adjusted under 35 U.S.C. 154(b) by 0 days.

(21) Appl. No.: 13/812,777

(22) PCT Filed: Jul. 22, 2011
(Under 37 CFR 1.47)

(86) PCT No.: PCT/US2011/045114
§ 371 (c)(1),
(2), (4) Date: Nov. 20, 2013

(87) PCT Pub. No.: WO2012/015704
PCT Pub. Date: Feb. 2, 2012

(65) Prior Publication Data
US 2013/0217764 A1    Aug. 22, 2013

Related U.S. Application Data

(60) Provisional application No. 61/368,500, filed on Jul. 28, 2010.

(51) Int. Cl.
*C07C 233/00* (2006.01)
*A61K 31/265* (2006.01)
*A61K 31/16* (2006.01)
(Continued)

(52) U.S. Cl.
CPC ........... *C07C 271/56* (2013.01); *C07C 2101/14* (2013.01)

(58) Field of Classification Search
USPC ........................... 564/123; 514/512, 613, 617
See application file for complete search history.

(56) References Cited

U.S. PATENT DOCUMENTS 5,541,061 A    7/1996   Fodor et al.
5,559,410 A    9/1996   Papazian et al.
(Continued)

FOREIGN PATENT DOCUMENTS

CN    100340556    9/2005
CN    1729171      2/2006
(Continued)

OTHER PUBLICATIONS

Vacondio, F. et al., ChemMedChem vol. 4 pp. 1495-1504. Published 2009.*
(Continued)

*Primary Examiner* — Paul Zarek
*Assistant Examiner* — George W Kosturko
(74) *Attorney, Agent, or Firm* — Mintz, Levin, Cohn, Ferris, Glovsky and Popeo, P.C.

(57) ABSTRACT

Peripherally restricted inhibitors of fatty acid amide hydrolase (FAAH) are provided. The compounds can suppress FAAH activity and increases anandamide levels outside the central nervous system (CNS). Despite their relative inability to access brain and spinal cord, the compounds attenuate behavioral responses indicative of persistent pain in rodent models of inflammation and peripheral nerve injury, and suppresses noxious stimulus-evoked neuronal activation in spinal cord regions implicated in nociceptive processing. CBi receptor blockade prevents these effects. Accordingly, the invention also provides methods, and pharmaceutical compositions for treating conditions in which the inhibition of peripheral FAAH would be of benefit. The compounds of the invention are according to the formula (I): in which $R_1$ is a polar group. In some embodiments, $R_1$ is selected from the group consisting of hydroxy and the physiologically hydrolysable esters thereof. $R_2$ and $R_3$ are independently selected from the group consisting of hydrogen and substituted or unsubstituted hydrocarbyl; each $R_4$ is independently selected from the group consisting of halogen and substituted or unsubstituted hydrocarbyl and n is an integer from 0 to 4; each $R_5$ is independently selected from the group consisting of halo and substituted or unsubstituted hydrocarbyl and m is an integer from 0 to 3; and $R_6$ is substituted or unsubstituted cyclohexyl; and the pharmaceutically acceptable salts thereof.

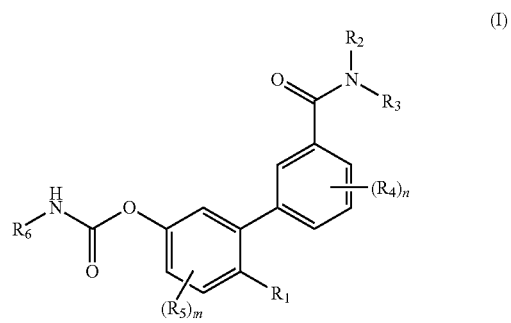

24 Claims, 29 Drawing Sheets

(51) Int. Cl.
A61K 31/165 (2006.01)
C07C 271/56 (2006.01)

(56) References Cited

U.S. PATENT DOCUMENTS

| | | | |
|---|---|---|---|
| 5,576,220 | A | 11/1996 | Hudson et al. |
| 5,962,012 | A | 10/1999 | Lin et al. |
| 6,261,595 | B1 | 7/2001 | Stanley et al. |
| 6,271,015 | B1 | 8/2001 | Gilula et al. |
| 6,326,156 | B1 | 12/2001 | Civelli et al. |
| 2002/0173550 | A1 | 11/2002 | Calignano et al. |
| 2003/0134894 | A1 | 7/2003 | Piomelli et al. |
| 2003/0149082 | A1 | 8/2003 | Makriyannis et al. |
| 2004/0127518 | A1 | 7/2004 | Piomelli et al. |
| 2007/0155707 | A1* | 7/2007 | Dasse et al. ............ 514/114 |

FOREIGN PATENT DOCUMENTS

| | | |
|---|---|---|
| CN | 1741990 | 3/2006 |
| CN | 1922162 | 2/2007 |
| WO | 98/20119 | 5/1998 |
| WO | WO 2004033422 A2 * | 4/2004 |
| WO | 2008/063714 | 5/2008 |
| WO | 2009/109504 | 9/2009 |
| WO | 2012/015704 | 2/2012 |

OTHER PUBLICATIONS

Vacondio, F. et al (ChemMedChem vol. 4, pp. 1495-1504, published 2009).*
Mor. Marco et al. 'Cyclohexylcarbamic Acid 3-or 4-Substituted Biphenyl-3-yl Esters as Fatty Acid Amide Hydrolase Inhibitors: Synthesis, Quantitative Structure-Activity Relationships, and Molecular Modeling Studies.' J. Med.Chem. 2004, vol. 47, pp. 4998-5008. See pp. 4999-5001, scheme 3a, and tables 1, 3.
Fegley, Darren et al. 'Characterization of the Fatty Acid Amide Hydrolase Inhibitor Cyclohexyl Carbamic Acid 3-carbamoyl-biphenyl-3-yl Ester URB597: Effects on Anadamide and Oleoylethanolamide deactivation.' Journal of Pharmacology and Experimental Therapeutics.2005, vol. 31, pp. 352-358. See abstract and figure 1a.
Ahn. Kyunghye et al .Novel Mechanistic Class of Fatty Acid Amide Hydrolase Inhibitors with Remarkable Selectivity.Biochemistry. 2007, vol. 46, pp. 13019-13030. See abstract and figure 1.
Niforatos, Wende et al.. 'Activation of TRPA1 Channels by the Fatty Acid Amide Hydrolase Inhibitor 3-Carbamoylbiphenyl-3-yl cyclohexylcarbamate (URB597).' Mol. Pharmacol. 2007, vol. 71, pp. 1209-1216. See abstract and figure 1A.
Piomelli, D., et al., *Proc. Natl. Acad. Sci. U.S.A.* (2002).
Piomelli, D., et al. *Trends Pharmacol. Sci.* 21, 218-224 (2000).
Nackley, A.G., Suplita, R.L., 2nd, & Hohmann, A.G., A peripheral cannabinoid mechanism suppresses spinal fos protein expression and pain behavior in a rat model of inflammation. Neuroscience 117 (3), 659-670 (2003).
Dziadulewicz, E.K. et al., Naphthalen-1-yl-(4-pentyloxynaphthalen-1-yl)methanone: a potent, orally bioavailable human CB1/CB2 dual agonist with antihyperalgesic properties and restricted central nervous system penetration. J Med Chem 50 (16), 3851-3856 (2007).
Agarwal, N. et al., Cannabinoids mediate analgesia largely via peripheral type 1 cannabinoid receptors in nociceptors. Nat Neurosci 10 (7), 870-879 (2007).
Kaufmann, I. et al., Enhanced anandamide plasma levels in patients with complex regional pain syndrome following traumatic injury: a preliminary report. Eur Surg Res 43 (4), 325-329 (2009).
Richardson, D. et al., Characterisation of the cannabinoid receptor system in synovial tissue and fluid in patients with osteoarthritis and rheumatoid arthritis. Arthritis Res Ther 10 (2), R43 (2008).
Mitrirattanakul, S. et al., Site-specific increases in peripheral cannabinoid receptors and their endogenous ligands in a model of neuropathic pain. Pain 126 (1-3), 102-114 (2006).

Schlosburg, J.E., Kinsey, S.G., & Lichtman, A.H., Targeting fatty acid amide hydrolase (FAAH) to treat pain and inflammation. AAPS J 11 (1), 39-44 (2009).
Kathuria, S. et al., Modulation of anxiety through blockade of anandamide hydrolysis. Nat Med 9 (1), 76-81 (2003).
Piomelli, D. et al., Pharmacological profile of the selective FAAH inhibitor KDS-4103 (URB597). CNS Drug Rev 12 (1), 21-38 (2006).
Clapper, J.R. et al., A second generation of carbamate-based fatty acid amide hydrolase inhibitors with improved activity in vivo. ChemMedChem 4 (9), 1505-1513 (2009).
Alexander, J.P. & Cravatt, B.F., Mechanism of carbamate inactivation of FAAH: implications for the design of covalent inhibitors and in vivo functional probes for enzymes. Chem Bioi 12 (11), 1179-1187 (2005).
LoVerme, J., La Rana, G., Russo, R., Calignano, A., & Piomelli, D., The search for the palmitoylethanolamide receptor. Life Sci 77 (14), 1685-1698 (2005).
Sagar, D.R., Kendall, D.A., & Chapman, V., Inhibition of fatty acid amide hydrolase produces PPAR-alpha-mediated analgesia in a rat model of inflammatory pain. Br J Pharmacol155 (8), 1297-1306 (2008).
Richardson, J.D., Kilo, S., & Hargreaves, K.M., Cannabinoids reduce hyperalgesia and inflammation via interaction with peripheral CB1 receptors. Pain 75 (1),111-119 (1998).
Mackie, K., Cannabinoid receptors as therapeutic targets. Annu Rev Pharmacol Toxicol 46, 101-122 (2006).
LoVerme, J. et al., Rapid broad-spectrum analgesia through activation of peroxisome proliferator-activated receptor-alpha. J Pharmacol Exp Ther 319 (3), 1051-1061 (2006).
Guindon, J. & Hohmann, A.G., Cannabinoid CB2 receptors: a therapeutic target for the treatment of inflammatory and neuropathic pain. Br J Pharmacol 153 (2), 319-334 (2008).
Cravatt, B.F. et al., Functional disassociation of the central and peripheral fatty acid amide signaling systems. Proc Natl Acad Sci US A 101 (29), 10821-10826 (2004).
Lever, I.J. et al., Localization of the endocannabinoid-degrading enzyme fatty acid amide hydrolase in rat dorsal root ganglion cells and its regulation after peripheral nerve injury. J Neurosci 29 (12), 3766-3780 (2009).
Tegeder, I. et al., Peripheral opioid analgesia in experimental human pain models. Brain 126 (Pt 5), 1092-1102 (2003).
Astarita, G., Ahmed, F., & Piomelli, D., Identification of biosynthetic precursors for the endocannabinoid anandamide in the rat brain. J Lipid Res 49 (1), 48-57(2008).
Russo, R. et al., The fatty acid amide hydrolase inhibitor URB597(cyclohexylcarbamic acid 3'-carbamoylbiphenyl-3-yl ester) reduces neuropathic pain after oral administration in mice. J Pharmacol Exp Ther 322 (1), 236-242 (2007).
Calignano, A., La Rana, G., & Piomelli, D., Antinociceptive activity of the endogenous fatty acid amide, palmitylethanolamide. Eur J Pharmacol 419 (2-3), 191-198 (2001).
Cadas, H., di Tomaso, E., & Piomelli, D., Occurrence and biosynthesis of endogenous cannabinoid precursor, N-arachidonoyl phosphatidylethanolamine, in rat brain. J Neurosci 17 (4), 1226-1242 (1997).
U.S. Appl. No. 61/368,500 filed Jul. 28, 2010.
International Search Report corresponding to the PCT/US2011/045114 application.
Office Action in Chinese corresponding application No. 201180046110.6.
Clapper, J.R. et al. (Oct. 2010, e-published Sep. 19, 2010). "Anandamide suppresses pain initiation through a peripheral endocannabinoid mechanism," *Nat Neurosci* 13(10):1265-1270.
Moreno-Sanz, G. et al. (Oct. 2011, e-published Jul. 7, 2011). "The ABC membrane transporter ABCG2 prevents access of FAAH inhibitor URB937 to the central nervous system," *Pharmacol Res* 64(4):359-363.
Tarzia, G. et al. (Jan. 2006). "Synthesis and structure-activity relationships of FAAH inhibitors: cyclohexylcarbamic acid biphenyl esters with chemical modulation at the proximal phenyl ring," *ChemMedChem* 1(10:130-139.

* cited by examiner

PERIPHERALLY RESTRICTED FAAH INHIBITORS

CROSS-REFERENCES TO RELATED APPLICATIONS

This application is the U.S. National Stage filing under 35 U.S.C. §371 of PCT/US2011/045114, filed Jul. 22, 2011, and claims priority benefit of U.S. Provisional Patent Application Ser. No. 61/368,500, filed on Jul. 28, 2010 the contents of which are incorporated herein by reference in its entirety for all purposes.

STATEMENT AS TO RIGHTS TO INVENTIONS MADE UNDER FEDERALLY SPONSORED RESEARCH AND DEVELOPMENT

This invention was made with Government support under Grant Nos. DA012413, DA012447 and AA017538 awarded by the National Institutes of Health. The U.S. Government has certain rights in this invention.

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Peripheral cannabinoid receptors exert a powerful inhibitory control over pain initiation, but the endogenous cannabinoid signal that normally engages this intrinsic analgesic mechanism is unknown. To address this question, we developed a peripherally restricted inhibitor of fatty acid amide hydrolase (FAAH), the enzyme responsible for the degradation of the endocannabinoid anandamide. The compound, called URB937, suppresses FAAH activity and increases anandamide levels outside the central nervous system (CNS). Despite its inability to access brain and spinal cord, URB937 attenuates behavioral responses indicative of persistent pain in rodent models of inflammation and peripheral nerve injury, and suppresses noxious stimulus-evoked neuronal activation in spinal cord regions implicated in nociceptive processing. $CB_1$ receptor blockade prevents these effects. The results suggest that anandamide-mediated signaling at peripheral $CB_1$ receptors controls the transmission of pain information to the CNS. Brain-impermeant FAAH inhibitors, which strengthen this gating mechanism, offer a new approach to pain therapy.

Anandamide, the naturally occurring amide of arachidonic acid with ethanolamine, meets all key criteria of an endogenous cannabinoid substance (Devane, W. A. et al. *Science,* 258, 1946-1949 (1992)): it is released upon demand by stimulated neurons (Di Marzo, V. et al., *Nature,* 372, 686-691 (1994); Giuffrida, A. et al., *Nat. Neurosci.,* 2, 358-363 (1999)); it activates cannabinoid receptors with high affinity (Devane, W. A. et al. *Science,* 258, 1946-1949 (1992)) and it is rapidly eliminated through a two-step process consisting of carrier-mediated transport followed by intracellular hydrolysis (Di Marzo, V. et al., *Nature,* 372, 686-691 (1994); Beltramo, M. et al., *FEBS Lett.,* 403, 263-267 (1997)). Anandamide hydrolysis is catalyzed by the enzyme fatty acid amide hydrolase (FAAH), a membrane-bound serine hydrolase (Cravatt, B. F. et al., *Nature,* 384, 83-87 (1996); Patricelli, M. P. et al., *Biochemistry,* 38, 9804-9812 (1999)) (WO 98/20119) (U.S. Pat. No. 6,271,015) that also cleaves other bioactive fatty ethanolamides, such as oleoylethanolamide(cis-9-octadecenamide)) (Rodriguez de Fonseca, F. et al. *Nature,* 414, 209-212 (2001)) and palmitoylethanolamide (Calignano, A. et al., *Nature,* 394, 277-281 (1998)). Mutant mice lacking the gene encoding for FAAH cannot metabolize anandamide (Cravatt, B. F. et al., *Proc. Natl. Acad. Sci. U.S.A.,* 98, 9371-9376 (2001)) and, though fertile and generally normal, show signs of enhanced anandamide activity at cannabinoid receptors, such as reduced pain sensation (Cravatt, B. F. et al., *Proc. Natl. Acad. Sci. U.S.A.,* 98, 9371-9376 (2001)). This suggests the possibility that drugs targeting FAAH may heighten the tonic actions of anandamide, while possibly avoiding the multiple, often unwanted effects produced by $\Delta^9$-THC and other direct-acting cannabinoid agonists (Hall, W., et al., *Lancet,* 352, 1611-1616 (1998); Chaperon, F., et al., *Crit. Rev. Neurobiol.,* 13, 243-281 (1999)).

Pain perception can be effectively controlled by neurotransmitters that operate within the CNS. This modulation has been well characterized in the dorsal horn of the spinal cord, where impulses carried by nociceptive (pain-sensing) fibers are processed before they are transmitted to the brain. In addition to these central mechanisms, intrinsic control of pain transmission can occur at terminals of afferent nerve fibers outside the CNS. One prominent example of peripheral regulation is provided by the endogenous opioids, which are released from activated immune cells during inflammation and inhibit pain initiation by interacting with opioid receptors localized on sensory nerve endings[1,2].

It has been proposed that endocannabinoid mediators might serve an analogous function to that of the opioids, because pharmacological activation of peripheral $CB_1$ and $CB_2$ cannabinoid receptors inhibits pain-related behaviors[3-7] while genetic disruption of $CB_1$ receptor expression in primary nociceptive neurons exacerbates such behaviors[8]. Moreover, there is evidence that clinical conditions associated with neuropathic pain or inflammation, such as complex regional pain syndrome and arthritis, may be accompanied by peripheral elevations in the levels of the endocannabinoid anandamide[9,10]. Another major endocannabinoid ligand, 2-arachidonoylglycerol (2-AG), has also been implicated in nociceptive signaling outside the CNS[8,11].

Much attention has been directed toward the role of anandamide in pain. Methods of treating pain by administering anandamide and palmitoylethanolamide are disclosed in U.S. Patent Application Publication No. 20020173550. Methods of treating pain by administering inhibitors of FAAH are disclosed in U.S. Patent Application Publication Nos. 20040127518 and 20030134894. Methods of treating pain by administering inhibitors of anandamide transport are disclosed in U.S. Patent Application Publication No. 20030149082.

Although these findings suggest that the endocannabinoid system serves an important function in the peripheral regulation of nociception, they offer no definitive insight on the identity of the endogenous ligand, or ligands, involved in this function. Filling this gap is essential, however, to gain a molecular understanding of the intrinsic mechanisms that control pain initiation and to discover new analgesic agents devoid of central side effects. In the present study we identified and characterized a brain-impermeant inhibitor of the anandamide-degrading enzyme, FAAH, with the aim of magnifying the actions of peripheral anandamide and unmasking their possible role in the control of emerging pain signals[12]. A particular concern in the development and therapeutic use of FAAH inhibitors is their ability to modulate endogenous cannabinoid systems within the CNS system to cause unwanted psychotropic or mood-altering effects.

The present invention addresses these and other needs by providing peripherally restricted FAAH inhibitors and method of their use in the treatment of a variety of conditions, including pain and/or inflammation.

BRIEF SUMMARY OF THE INVENTION

In a first aspect, the invention provides compounds, and pharmaceutical compositions of the compounds, having the formula:

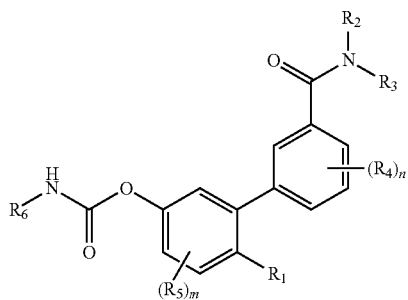

in which $R_1$ is selected from the group consisting of hydroxy and the physiologically hydrolyzable esters thereof, —SH, —O-carboxamido, —OC(O)$R_7$, —O—CO—$NR_8R_9$ and —$NR_8R_9$, wherein $R_7$ is substituted or unsubstituted hydrocarbyl and $R_8$ and $R_9$ are independently selected from the group consisting of hydrogen and ($C_1$-$C_3$)alkyl; $R_2$ and $R_3$ are independently selected from the group consisting of hydrogen and hydrocarbyl; each $R_4$ is independently selected from the group consisting of halogen and hydrocarbyl and n is an integer from 0 to 4; each $R_5$ is independently selected from the group consisting of halo and hydrocarbyl and m is an integer from 0 to 3; and $R_6$ is substituted or unsubstituted cyclohexyl; and the pharmaceutically acceptable salts thereof. In preferred embodiments, the compounds are peripherally restricted in their distribution in a recipient.

In a second aspect, the invention provides pharmaceutical compositions comprising a therapeutically effective amount of the compounds according to the invention. The compositions can be formulated for any route of administration including the oral and parenteral routes. In addition, the compositions may be in a unit dose format.

In a third aspect, the invention provides a method of treating a subject in need of a peripherally restricted FAAH inhibitor (e.g., a FAAH inhibitory compound according to the invention). In preferred embodiments, the subject is a human. In some embodiments, the need is with respect to a treatment for pain, inflammation, or an immune disorder of the subject. In some embodiments, the pain can be nociceptive, inflammatory, or neuropathic pain. Preferably, the peripherally restricted FAAH inhibitory compound is a compound of the invention.

In a fourth aspect, the invention provides a method of enhancing the peripheral activity of an endogenously produced (i.e., an endocannabinoid such as anandamide, N-arachidonoyl dopamine) or exogenously provided cannabinoid fatty acid amide in a subject by administering a compound according to the invention. Preferably, the fatty acid amide is anandamide, N-arachidonoyl dopamine, oleoylethanolamide, stearoylethanolamide, or palmitoylethanolamide. Where the fatty ethanolamide is exogenously provided, the fatty acid ethanolamide can be administered to the subject before, after, or contemporaneous with the administration of the compound according to the invention. In some embodiments, the subject is in need of treatment for pain, inflammation, or an immune disorder. In preferred embodiments, the pain can be nociceptive, inflammatory, or neuropathic pain.

In a fifth aspect, the invention provides methods of screening compounds for their ability to be extruded from brain via the breast cancer resistance protein (BCRP) transport system. Scaffolds similar to that of URB937 and the compounds according to the invention can serve as substrates for BCRP. Accordingly, in some embodiments the invention provides methods of assaying an URB937 analog and/or compounds according to the invention based on their ability to be transported by the BCRP transport system in vitro.

DETAILED DESCRIPTION OF THE INVENTION

Figure 1A:
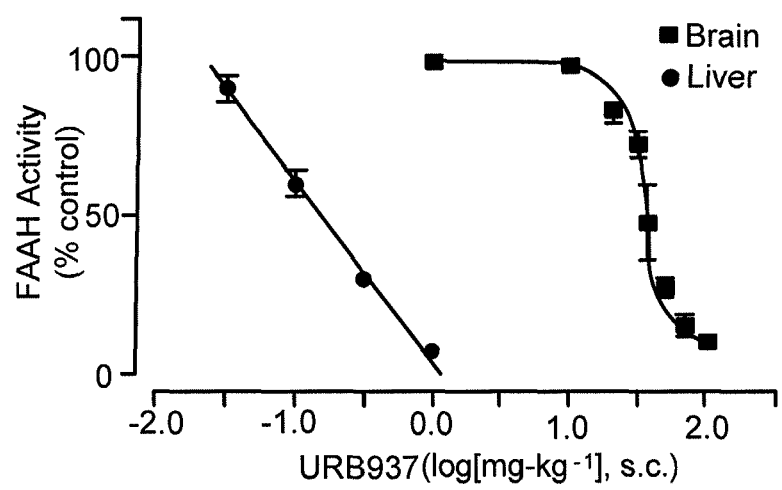
FIG. 1 URB937 is a peripherally restricted FAAH inhibitor. (a) FAAH activity in liver (closed circles) and brain (closed squares) 1 h after administration of various doses of URB937 (0.03-100 mg-kg$^{-1}$, s.c.) in Swiss mice. (b) Distribution of URB937 in liver (closed circles), brain (closed squares) and serum (inset) after a single injection in mice (1 mg-kg$^{-1}$, i.p.). (c) Time-course of inhibition of FAAH activity in liver (closed circles) or brain (closed squares) after administration of URB937 (1 mg-kg$^{-1}$, i.p.). (d) Effects of URB937 (1 mg-kg$^{-1}$, i.p., closed bars) or vehicle (open bars) on anandamide and palmitoylethanolamide (PEA) levels in liver, forebrain and hypothalamus of Swiss mice. (e) Effects of URB937 on anandamide and PEA levels in liver of wild-type C57Bl/6 mice (+/+) and FAAH-deficient mice (−/−). (f) Lack of effect of URB937 (1 mg-kg$^{-1}$, i.p., closed bars) on 2-arachidonoylglycerol (2-AG) levels in Swiss mice. Results are expressed as mean±sem; n=3; *P<0.05; ***P<0.001 vs vehicle.

Peripheral cannabinoid receptors exert a powerful inhibitory control over pain initiation, but the endogenous cannabinoid signal that normally engages this intrinsic analgesic mechanism is unknown. We developed a novel peripherally restricted inhibitor of fatty acid amide hydrolase (FAAH), the enzyme responsible for the degradation of the endocannabinoid anandamide. The compound, called URB937, suppresses FAAH activity and increases anandamide levels outside the central nervous system (CNS). Despite a surprising relative inability (the compound is also surprisingly susceptible to a transport system mediated extrusion from brain) to access brain and spinal cord, URB937 attenuates behavioral responses indicative of persistent pain in rodent models of inflammation and peripheral nerve injury, and suppresses noxious stimulus-evoked neuronal activation in spinal cord regions implicated in nociceptive processing. $CB_1$ receptor blockade prevents these effects. The results indicate that anandamide-mediated signaling at peripheral $CB_1$ receptors controls the transmission of pain information to the CNS. Relatively brain-impermeant FAAH inhibitors, which strengthen this gating mechanism, might offer a new approach to pain therapy.

Pain perception can be effectively controlled by neurotransmitters that operate within the CNS. This modulation has been well characterized in the dorsal horn of the spinal cord, where impulses carried by nociceptive (pain-sensing) fibers are processed before they are transmitted to the brain. In addition to these central mechanisms, intrinsic control of pain transmission can occur at terminals of afferent nerve fibers outside the CNS. One prominent example of peripheral regulation is provided by the endogenous opioids, which are released from activated immune cells during inflammation and inhibit pain initiation by interacting with opioid receptors localized on sensory nerve endings[1,2].

The compound URB937 is a potent FAAH inhibitor that does not readily enter the CNS and thus principally interrupts anandamide deactivation only in peripheral tissues. Despite this restricted range of action, URB937 causes marked antinociceptive effects in rodent models of acute and persistent pain, which are prevented by $CB_1$ cannabinoid receptor blockade. These findings suggest that inhibition of peripheral FAAH activity magnifies an endogenous analgesic mechanism which regulates the transmission of emerging nociceptive inputs to the spinal cord and the brain. The mechanism is likely to be mediated by anandamide or another endogenous fatty acid amide cannabinoid.

Without being wed to theory, peripheral anandamide signaling is thought to serve as a diffuse paracrine system that modulates the intensity of pain stimuli as they arise in damaged tissues. Two lines of evidence support this idea. First, signals generated by inflammation and neural injury can trigger the local release of anandamide. For example, membrane depolarization and activation of TRPV-1 channels each stimulates anandamide production in cultures of sensory neurons[25], while activation of the pro-inflammatory receptor, Toll-like receptor 4, causes a similar effect in macrophages[26]. These signals, and probably others that remain to be identified, may contribute to the elevations in peripheral anandamide documented in animal models of spinal nerve injury and inflammation[8,11] as well as in painful human conditions such as complex regional pain syndrome[9] and arthritis[10]. Second, though particularly abundant in the brain, $CB_1$ receptors are broadly distributed throughout mammalian tissues and organs. In particular, they are expressed in large-sized primary sensory neurons and are transported to peripheral nerve endings[27,28], where they may be both necessary to maintain normal pain thresholds[8] and sufficient to exert marked antinociceptive effects[3,6]. $CB_1$ receptors on pain-sensing terminals may mediate the analgesic actions of locally produced anandamide, and might also be implicated in the anti-inflammatory activity of this lipid mediator through their inhibitory influence on the release of excitatory neuropeptides[29]. Nevertheless, it is reasonable to assume that other cannabinoid and cannabinoid-like receptors also contribute, directly or indirectly, to anandamide signaling in response to injury. Two likely candidates are $CB_2$ receptors, which can be activated either by anandamide or 2-AG[30], and type-a peroxisome proliferator-activated receptors, which are activated by PEA and other lipid-derived mediators[7,20,21]. These receptors and their endogenous ligands are present in peripheral sensory neurons and immune cells, and have been implicated in the modulation of nociception and inflammation[21,31,32].

Mutant mice in which FAAH is selectively deleted in non-neuronal cells, but is preserved in peripheral and central neurons, display a striking phenotype in which normal nociceptive transmission is accompanied by reduced responsiveness to proinflammatory triggers[33]. A possible explanation for this finding, which is consistent with the present results, is that the signaling activity of anandamide at peripheral nociceptors is regulated by FAAH localized to the nociceptors themselves, rather than to neighboring non-neural cells. This is consistent with the observation that peripheral axotomy induces FAAH expression in large-sized sensory neurons, a response that is expected to expand the colocalization of FAAH with $CB_1$ receptors[34].

Direct-acting agonists of opioid receptors exert profound analgesic effects in animal and human experimental pain models[2,35]. Our results indicate that is possible to achieve significant analgesia also by magnifying the activity of an anandamide-based mechanism involved in maintaining nociceptive homeostasis. These findings provide new insights into the intrinsic control of pain and can be exploited therapeutically to develop effective analgesics largely devoid of central side effects.

Definitions

It is noted here that as used in this specification and the appended claims, the singular forms "a," "an," and "the" include plural reference unless the context clearly dictates otherwise.

"FAAH" denotes a mammalian Fatty Acid Amide Hydrolase and includes, but is not limited to, the human, rat, and mouse forms of the enzyme. U.S. Pat. No. 6,271,015 discloses isolated and purified forms of FAAH. In one set of embodiments, the FAAH $IC_{50}$ of the subject compounds is defined according to inhibition of the rat enzyme under physiologically relevant conditions. Fatty Amide Hydrolases (FAAHs) (Deutsch, D. G., et al., *Prostaglandins Leukot. Essent. Fatty Acid,* 66, 201-210 (2002)) are enzymes responsible for the degradation of lipid ethanolamides, (Fowler, C. J., et al., *Biochem. Pharmacol.* 62, 517-526 (2001); Patricelli, M. P., et al. *Vitam. Horm.,* 62, 663-674 (2001)) e.g. anandamide (AEA, 1, FIG. 1), (Devane, W. A., et al., *Science* 258, 1946-1949 (1992)) oleoylethanolamide, (Rodriguez de Fonseca, F., et al. *Nature* (London) 414, 209-212 (2001); Fu, J., et al., *Nature* (London) 425, 90-93 (2003)) and palmitoylethanolamide, (Calignano, A., et al. *Nature* (London) 394, 277-281 (1998); Lambert, D. M., et al., *Curr. Med. Chem.* 9, 663-674 (2002)) a biochemical process which, along with selective trasport into cells in the case of AEA, (Di Marzo, V., *Nature* (London) 372, 686-691 (1994); Beltrama, M., et al., *Science* 277, 1094-1097 (1997); Piomelli, D., et al., *Proc. Natl. Acad. Sci. U.S.A.* (2002)) brings about the cessation of the cellular effects of these autacoids. Owing to the various and important physiological roles of fatty acid ethanolamides, classes of small-molecule compounds able to block FAAH or FAAHs but not bind to other endocannabinoid-metabolizing enzymes, e.g. monoglyceride lipase (MGL), (Dinh, T. P., et al., *Proc. Natl. Acad. Sci. U.S.A.* 99, 10819-10824 (2002)) or cannabinoid receptors, would be advantageous both as pharmacological tools and as prototypes for drug development projects (Piomelli, D., et al. *Trends Pharmacol. Sci.* 21, 218-224 (2000); Bisogno, T., et al., *Curr. Pharm. Des.* 8, 533-547 (2002); Yarnell, A., *Chem. Eng. News* 80(49), 32 (2002); Smith, A., *Nat. Rev. Drug Discov.* 2, 92 (2003); Wendeler, M., et al. *Angew. Chem. Int. Ed.* 42, 2938-2941 (2003)).

The term "pharmaceutically acceptable carrier" encompasses any of the standard pharmaceutical carriers, buffers and excipients, including phosphate-buffered saline solution, water, and emulsions (such as an oil/water or water/oil emulsion), and various types of wetting agents and/or adjuvants. Suitable pharmaceutical carriers and their formulations are described in Remington's Pharmaceutical Sciences (Mack Publishing Co., Easton, 19th ed. 1995). Preferred pharmaceutical carriers depend upon the intended mode of administration of the active agent. Typical modes of administration are described below.

The term "effective amount" means a dosage sufficient to produce a desired result with respect to the indicated disorder, condition, or mental state. The desired result may comprise a subjective or objective improvement in the recipient of the dosage. With respect to pain, the improvement may be decreased sign or symptom of pain.

The terms "treatment", "therapy" and the like include, but are not limited to, methods and manipulations to produce beneficial changes in a recipient's health status. The changes can be either subjective or objective and can relate to features such as symptoms or signs of the disease, disorder or condition being treated. For example, if the patient notes decreased pain, then successful treatment of pain has occurred. For example, if a decrease in the amount of swelling has occurred, then a beneficial treatment of inflammation has occurred. Similarly, if the clinician notes objective changes, such as improved range of motion, then treatment for a pain or inflammation which had been impairing the motion has also been beneficial. Preventing the deterioration of a recipient's status is also included by the term.

Therapeutic benefit includes any of a number of subjective or objective factors indicating a beneficial response or improvement of the condition being treated as discussed herein.

"Pharmaceutically-acceptable" or "therapeutically-acceptable" refers to a substance which does not interfere with the effectiveness or the biological activity of the active ingredients and which is not toxic to the hosts in the amounts used, and which hosts may be either humans or animals to which it is to be administered.

"Therapeutically-effective amount" refers to the amount of an active agent sufficient to induce a desired biological or clinical result. That result may be alleviation of the signs, symptoms, or causes of a disease, or any other desired alteration of a biological system. The term "therapeutically effective amount" is used herein to denote any amount of the formulation which causes a substantial improvement in a disease, disorder or condition when administered to a subject. The amount will vary with the condition being treated, the stage of advancement of the condition, and the type and concentration of formulation applied. Appropriate amounts in any given instance will be readily apparent to those skilled in the art or capable of determination by routine experimentation.

A "prophylactic treatment" is a treatment administered to a subject who does not exhibit signs of a neurological or psychological disorder or condition or exhibits only early or slight signs of such a disorder or condition, wherein treatment is administered for the purpose of decreasing the risk of developing a pathology or worsening of disorder or condition. The compounds of the invention may be given as a prophylactic treatment to prevent undesirable or unwanted anxiety or panic attacks, or to reduce the level of anxiety should worsening occur.

The term "subject" as used herein includes any animal, including, but not limited to, mammals (e.g., rat, mouse, cat, dog) including humans to which a treatment is to be given.

As used herein, the term "hydrocarbyl" refers to a $(C_1-C_8)$ hydrocarbon radical that is a $(C_1-C_8)$alkyl, $(C_1-C_8)$alkenyl, ($C_3$-$C_8$)cycloalkyl, ($C_3$-$C_8$)cycloalkenyl, ($C_1$-$C_8$)heteroalkyl, ($C_1$-$C_8$)heteroalkenyl, ($C_3$-$C_8$)heterocycloalkyl, or ($C_3$-$C_8$)heterocycloalkenyl radical. More preferably, the hydrocarbyl in each instance is a substituted or unsubstituted ($C_1$ to $C_6$), ($C_1$ to $C_3$), or ($C_1$ to $C_2$)hydrocarbyl, and more preferably still an unsubstituted ($C_1$ to $C_3$)alkyl. Still more preferably the hydrocarbyl in each instance is methyl or ethyl or trifluoromethyl. The term "hydrocarbyl" also includes those groups having up to 1, 2, or 3 atoms of a hydrocarbyl group as set forth above replaced by a heteroatom with the proviso that the heteroatoms of the hydrocarbyl are not contiguous to each other and the hydrocarbyl is not attached to the remainder of the compound by a heteroatom of the hydrocarbyl.

As used herein, the term "alkyl", by itself or as part of another substituent, means, unless otherwise stated, a straight or branched chain, saturated, hydrocarbon radical, having the number of carbon atoms designated (i.e. ($C_1$-$C_6$) means one to six carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like.

As used herein, the term "alkoxy" represents an alkyl moiety joined to the remainder of the molecule by the oxygen atom of the alkoxy. Accordingly, examples of alkoxy would include, but not be limited to, methoxy, ethoxy, propoxy and the like.

The term "alkenyl" is derived from the name of the corresponding alkyl group but differs in possessing one or more double bonds. Similarly, "alkynyl" groups are named with respect to their corresponding alkyl group but differs in possessing one or more triple bonds. Non-limiting examples of such unsaturated alkenyl groups and alkynyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

As used herein, the term "heteroalkyl" derives its name from the corresponding alkyl group but differs in containing one, two, or three heteroatoms independently selected from N, O, and S each substituting for a carbon of an alkyl group. The heteroatom nitrogen and sulfur atoms are optionally oxidized, and the nitrogen atom(s) are optionally quaternized. A heteroalkyl group is attached to the remainder of the molecule through a carbon atom of the heteroalkyl group and the heteroatoms of the heteroalkyl are not contiguous with another heteroatom.

The term "heteroalkenyl" derives its name from the corresponding alkenyl group but differs in having 1, 2, or 3 heteroatoms substituting for a carbon of the alkenyl group. The heteroatom nitrogen and sulfur atoms are optionally oxidized, and the nitrogen atom(s) are optionally quaternized. A heteroatom can form a double bond with a carbon atom. A heteroalkenyl group is attached to the remainder of the molecule through a carbon atom of to hydrocarbyl and the heteroatoms of the hydrocarbyl are not contiguous with another heteroatom.

As used herein, the term "cycloalkyl" refers to a saturated monocyclic hydrocarbon radical comprising from about 3 to about 8 carbon atoms, and more preferably 3 to 6 carbon atoms. The term "cycloalkenyl" refers to monocyclic, non-aromatic hydrocarbon radical comprising from about 5 to about 6 carbon atoms and having at least one double bond. Exemplary cycloalkyl groups and cycloalkenyl groups include cyclopropyl, cyclobutyl, cyclopentyl, cyclohexyl, cyclohexenyl, cyclohepta-1,3-dienyl, and the like.

As used herein, the term "heterocycloalkyl" refers to a saturated or partially unsaturated monocyclic hydrocarbon radical comprising from about 3 to about 8 carbon atoms, and more preferably 3 to 6 carbon atoms in which 1, 2 or 3 of the carbon atoms are independently replaced by a heteroatom independently selected from O, N, or S. Nitrogen and sulfur atoms are optionally oxidized, and the nitrogen atom(s) are optionally quaternized. Sulfur maybe in the thio, sulfinyl or sulfonyl oxidation state. The term "heterocycloalkenyl" refers to heterocycloalkyl group having at least one double bond. A heterocycloalkyl or heterocycloalkenyl group is attached to the remainder of the molecule through a carbon atom, respectively, of the heterocycloalkyl or heterocycloalkenyl group; and the heteroatoms of the heterocycloalkyl or heterocycloalkenyl are not contiguous with another heteroatom of the heterocycloalkyl or heterocycloalkenyl.

As used herein, the term "heteroatom" is meant to include oxygen (O), nitrogen (N), and sulfur (S)).

As used herein, the term "halogen" or "halo" refers to iodine (I), bromine (Br), chlorine (Cl), and/or fluorine (F).

The above hydrocarbyl, alkyl, alkenyl, cycloalkyl, cycloalkenyl, heteroalkyl, heteroalkenyl, cycloheteroalkyl, and cycloheteroalkenyl radicals can each be substituted with one, two or three substituents independently selected from unsubstituted ($C_1$-$C_6$) or ($C_1$-$C_3$)alkyl, unsubstituted ($C_1$-$C_6$) or ($C_1$-$C_3$)alkoxy, unsubstituted amino, unsubstituted ($C_1$-$C_6$) or ($C_1$-$C_3$) alkylamino, di-unsubstituted ($C_1$-$C_6$) or ($C_1$-$C_3$)alkylamino, hydroxy, halo, unsubstituted carboxamido, unsubstituted ($C_1$-$C_6$) or ($C_1$-$C_3$)alkylcarboxamido, oxo, and nitro. Non-limiting examples of alkoxy groups include methoxy, ethoxy, t-butoxy, cyclopentyloxy, trifluoromethoxy, and the like. As used herein, the term "oxo" refers to =O. As used herein, the term "amino" refers to —$NH_2$. In some embodiments, each of the hydrocarbyl groups are unsubstituted. In some embodiments, each of the hydrocarbyl, alkyl, alkenyl, cycloalkyl, cycloalkenyl, heteroalkyl, heteroalkenyl, cycloheteroalkyl, and cycloheteroalkenyl groups are unsubstituted.

A peripherally restricted compound is one which poorly penetrates the blood brain barrier or is extruded more rapidly from the brain. Accordingly, a peripherally restricted compound according to the invention can be administered at dosages which inhibit FAAH activity in the periphery to a far greater extent than centrally (e.g., in brain). In some embodiments, the FAAH inhibitor according to the invention has a subcutaneously, intravenously, or orally administered $ED_{50}$ for inhibiting peripheral FAAH activity (e.g., liver) which is no more than ¼, ⅛, or 1/10 of the $ED_{50}$ for inhibiting brain FAAH activity in the mouse. Preferably, the peripherally restricted FAAH inhibitor is one which reduces FAAH activity in the periphery by at least 3, 4, 5, 7-, 8-fold, or 10-fold more than it reduced FAAH activity centrally (e.g., in the brain) of the test mammal. For instance, FAAH activity levels in the periphery can be inhibited by 80% (20% of the baseline or uninhibited level of FAAH activity remains) while central FAAH activity would be inhibited by 10% (90% of the baseline or uninhibited level of FAAH activity remains) providing for a 80%/10% or 8-fold difference in FAAH inhibition.

A physiologically cleavable ester is one which is a substrate for carboxyesterases in vivo. Physiologically cleavable esters are typically rapidly hydrolyzed such that the concentration of the corresponding alcohol comes to exceed that of the ester in blood or plasma. For instance, a physiologically cleavable ester is one which is rapidly hydrolyzed to the corresponding alcohol and acid in vivo with a half time of less than ½, 1, 2 or 3 hours at a therapeutically relevant dosages.

Compounds of the Invention

The compounds of the invention are according to the formula:

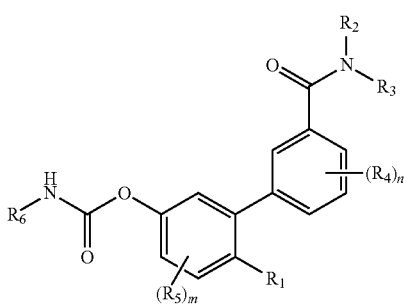

I in which $R_1$ is a polar group. In some embodiments, $R_1$ is selected from the group consisting of hydroxy and the physiologically hydrolysable esters thereof, —SH, —O-carboxamido, —OC(O)$R_7$, —O—CO—$NR_8R_9$ and —$NR_8R_9$, wherein $R_7$ is substituted or unsubstituted hydrocarbyl and $R_8$ and $R_9$ are independently selected from the group consisting of hydrogen and substituted or unsubstituted hydrocarbyl; $R_2$ and $R_3$ are independently selected from the group consisting of hydrogen and substituted or unsubstituted hydrocarbyl; each $R_4$ is independently selected from the group consisting of halogen and substituted or unsubstituted hydrocarbyl and n is an integer from 0 to 4; each $R_5$ is independently selected from the group consisting of halo and substituted or unsubstituted hydrocarbyl and m is an integer from 0 to 3; and $R_6$ is substituted or unsubstituted cyclohexyl; and the pharmaceutically acceptable salts thereof. In some embodiments each of $R_2$, $R_3$, $R_7$, $R_8$, and $R_9$ are independently selected from hydrogen and unsubstituted hydrocarbyl. In some further embodiments, each of $R_2$, $R_3$, $R_7$, $R_8$, and $R_9$ are independently hydrogen or unsubstituted $C_1$ to $C_3$ hydrocarbyl. In some further embodiments, each $R_4$ and $R_5$ member are independently halogen or $C_1$ to $C_3$ hydrocarbyl. Preferably, the above compounds of the invention are peripherally restricted.

In some further embodiments that are applicable to any of the above, m is 0 and n is 0, 1, 2, 3, or 4. In other further embodiments, m is 1 and n is 0, 1, 2, 3, or 4. In still other embodiments, m is 2 and n is 0, 1, 2, 3, or 4. In yet still further embodiments, m is 3, and n is 0, 1, 2, 3, or 4. In some further embodiments, the sum of m and n is 0, 1, 2, or 3. In still further embodiments, of each of the above, each hydrocarbyl member is unsubstituted.

Preferably, $R_1$ is hydroxy or a physiologically hydrolysable ester of the hydroxy. These esters include those of the formula —OC(O)$R_7$ wherein $R_7$ is substituted or unsubstituted hydrocarbyl, more preferably, substituted or unsubstituted alkyl, alkenyl, cycloalkyl, heteroalkyl, heterocycloalkyl, heteroalkenyl, heterocycloalkenyl, and cycoalkenyl and still more preferably, substituted or unsubstituted ($C_1$-$C_3$) alkyl (e.g., methyl, ethyl, propyl, trifluoromethyl) or a substituted or unsubstituted ($C_1$-$C_3$) hydrocarbyl selected from alkenyl, cycloalkyl, heteroalkyl, heterocycloalkyl, heteroalkenyl, heterocycloalkenyl, and cycoalkenyl. In further of these embodiments, m is 0 and n is 0, 1, 2; m is 1 and n is 0, 1, or 2; or m is 2 and n is 0, 1, or 2.

In further embodiments that are applicable to any of the above, $R_2$ and $R_3$ are hydrogen or a substituted or unsubstituted ($C_1$-$C_3$)hydrocarbyl selected from alkyl, alkenyl, cycloalkyl, heteroalkyl, heterocycloalkyl, heteroalkenyl, heterocycloalkenyl, and cycoalkenyl. In further of these embodiments, m is 0 and n is 0, 1, or 2; m is 1 and n is 0, 1, or 2; or m is 2 and n is 0, 1, or 2. In some further embodiments of such, at least one or both of $R_2$ and $R_3$ is hydrogen. In further of these embodiments, m is 0 and n is 0, 1, 2; m is 1 and n is 0, 1, or 2; or m is 2 and n is 0, 1, or 2. In still further embodiments, the $R_2$ and/or $R_3$ hydrocarbyl member is unsubstituted.

In further embodiments that are applicable to any of the above, $R_1$ is hydroxy and at least one of $R_2$ and $R_3$ is hydrogen. In still further embodiments of such, both of $R_2$ and $R_3$ are hydrogen. In other embodiments in which $R_1$ is hydroxy, $R_2$ and $R_3$ are independently selected from substituted or unsubstituted ($C_1$-$C_3$)alkyl (e.g., methyl, ethyl, propyl), and H. In further of these embodiments, m is 0 and n is 0, 1, 2; m is 1 and n is 0, 1, 2; or m is 2 and n is 0, 1, 2.

In yet still further embodiments that are applicable to any of the above, $R_6$ is substituted or unsubstituted cyclohexyl. Substituents for the cyclohexyl include alkyl (e.g., methyl, ethyl), halo (F, Cl, I, Br and preferably F or Cl), and trifluoromethyl. In yet other of these embodiments, m is 0 and n is 0, 1, 2; m is 1 and n is 0, 1, 2; or m is 2 and n is 0, 1, 2.

In other embodiments that are applicable to any of the above, $R_4$ is substituted or unsubstituted alkyl, alkenyl, cycloalkyl, heteroalkyl, heterocycloalkyl, heteroalkenyl, heterocycloalkenyl, or cycloalkenyl and still more preferably, substituted or unsubstituted ($C_1$-$C_3$)alkyl (e.g., methyl, ethyl, propyl, trifluoromethyl) or a substituted or unsubstituted ($C_1$-$C_3$) hydrocarbyl selected from alkenyl, cycloalkyl, heteroalkyl, heterocycloalkyl, heteroalkenyl, heterocycloalkenyl, and cycoalkenyl. In other embodiments, $R_4$ is selected from ($C_1$-$C_3$)alkyl (e.g., methyl, ethyl, propyl), and n is 0, 1, 2, or 3. In still further such embodiments, each $R_4$ is halogen or haloalkyl (e.g., trifluoromethyl). In yet further such embodiments, each $R_4$ is halogen or unsubstituted ($C_1$-$C_3$) alkyl (e.g., methyl, ethyl, propyl). In further such embodiments, m is 0 or 1.

In other embodiments that are applicable to any of the above, $R_5$ is substituted or unsubstituted alkyl, alkenyl, cycloalkyl, heteroalkyl, heterocycloalkyl, heteroalkenyl, heterocycloalkenyl, or cycloalkenyl and still more preferably, substituted or unsubstituted ($C_1$-$C_3$)alkyl (e.g., methyl, ethyl, propyl, trifluoromethyl) or a substituted or unsubstituted ($C_1$-$C_3$) hydrocarbyl selected from alkenyl, cycloalkyl, heteroalkyl, heterocycloalkyl, heteroalkenyl, heterocycloalkenyl, and cycoalkenyl. In other embodiments of any of the above, $R_5$ is selected from ($C_1$-$C_3$)alkyl (e.g., methyl, ethyl, propyl), and m is 1, 2, or 3. In still further such embodiments, each $R_5$ is halogen or haloalkyl (e.g., trifluoromethyl). In still further such embodiments, each $R_5$ is halogen or unsubstituted ($C_1$-$C_3$)alkyl (e.g., methyl, ethyl, propyl). In further such embodiments, n is 0 or 1.

In a particularly preferred embodiment, $R_1$ is hydroxy or a physiologically hydrolyzable ester thereof in which the hydrolysis releases the corresponding compound wherein $R_1$ is hydroxy, $R_6$ is unsubstituted cyclohexyl, m is 0 and n is 0, 1, or 2; or m is 1 and n is 0, 1, or 2, or m is 2 and n is 0, 1, or 2. In some embodiments of such the ester is of the formula —OC(O)$R_7$ wherein $R_7$ is substituted or unsubstituted hydrocarbyl, more preferably, substituted or unsubstituted alkyl, alkenyl, cycloalkyl, heteroalkyl, heterocycloalkyl, heteroalkenyl, heterocycloalkenyl, and cycoalkenyl and still more preferably, substituted or unsubstituted ($C_1$-$C_3$)alkyl (e.g., methyl, ethyl, propyl, trifluoromethyl) or a substituted or unsubstituted ($C_1$-$C_3$) hydrocarbyl selected from alkenyl, cycloalkyl, heteroalkyl, heterocycloalkyl, heteroalkenyl, heterocycloalkenyl, and cycoalkenyl. In some further embodiments, $R_7$ is unsubstituted hydrocarbyl, unsubstituted alkyl, unsubstituted alkenyl, unsubstituted cycloalkyl, unsubstituted heteroalkyl, unsubstituted heterocycloalkyl, unsubstituted heteroalkenyl, unsubstituted heterocycloalkenyl, or unsubstituted cycoalkenyl; or unsubstituted ($C_1$-$C_3$)alkyl (e.g., methyl, ethyl, propyl, trifluoromethyl) or unsubstituted ($C_1$-$C_3$) hydrocarbyl selected from alkenyl, cycloalkyl, heteroalkyl, heterocycloalkyl, heteroalkenyl, heterocycloalkenyl, and cycoalkenyl.

In a particularly preferred embodiment, the compound has the formula:

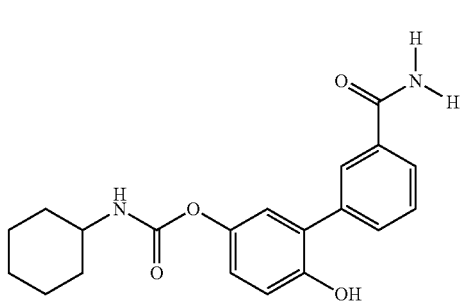

II

3'-carbamoyl-6-hydroxybiphenyl-3-yl cyclohexylcarbamate or is a physiologically hydrolyzable ester thereof in which the hydrolysis releases 3'-carbamoyl-6-hydroxybiphenyl-3-yl cyclohexylcarbamate and the pharmaceutically acceptable salts thereof.

In preferred embodiments, any of the above compounds are peripherally restricted compounds.

Compounds of the invention may contain one or more asymmetric centers and can thus occur as racemates and racemic mixtures, single enantiomers, diastereomeric mixtures and individual diastereomers. The present invention is meant to comprehend all such isomeric forms of the inventive compounds.

Compounds of the invention include any diastereoisomers or pairs of any enantiomers. Diastereomers for example, can be obtained by fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of such a compound of the invention may be obtained by stereospecific synthesis using optically pure starting materials of known configuration.

The compounds of the present invention may have unnatural ratios of atomic isotopes at one or more of their atoms. For example, the compounds may be radiolabeled with isotopes, such as tritium or carbon-14. All isotopic variations of the compounds of the present invention, whether radioactive or not, are within the scope of the present invention.

The instant compounds may be isolated in the form of their pharmaceutically acceptable acid addition salts, such as the salts derived from using inorganic and organic acids. Such acids may include hydrochloric, nitric, sulfuric, phosphoric, formic, acetic, trifluoroacetic, propionic, maleic, succinic, malonic and the like. In addition, certain compounds containing an acidic function can be in the form of their inorganic salt in which the counterion can be selected from sodium, potassium, lithium, calcium, magnesium and the like, as well as from organic bases. The term "pharmaceutically acceptable salts" refers to salts prepared from pharmaceutically acceptable non-toxic bases or acids including inorganic bases or acids and organic bases or acids.

The invention also encompasses prodrugs of the present compounds, which on administration undergo chemical conversion by metabolic processes before becoming active pharmacological substances. In general, such prodrugs will be derivatives of the present compounds that are readily convertible in vivo into a functional compound of the invention. Conventional procedures for the selection and preparation of suitable prodrug derivatives are described, for example, in "Design of Prodrugs", ed. H. Bundgaard, Elsevier, 1985. The invention also encompasses active metabolites of the present compounds.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed by the inventive Formulas.

High Throughput FAAH Inhibition Assays

The assays for compounds described herein are amenable to high throughput screening. Preferred assays thus detect binding of the inhibitor to FAAH or the release of a reaction product (e.g., fatty acid amide or ethanolamine) produced by the hydrolysis of a substrate such as oleoylethanolamide or anandamide. The substrate may be labeled to facilitate detection of the released reaction products. High throughput assays for the presence, absence, or quantification of particular reaction products are well known to those of skill in the art. Thus, for example, U.S. Pat. No. 5,559,410 discloses high throughput screening methods for proteins, and U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

Methods for Screening Compounds for Antinociceptive Activity.

Methods for screening FAAH inhibitors for an antinociceptive effect are well known to one of ordinary in the art. For instance, the test compounds can be administered to the subject animals in the mouse hot-plate test and the mouse formalin test and the nociceptive reactions to thermal or chemical tissue damage measured. See also U.S. Pat. No. 6,326,156 which teaches methods of screening for antinociceptive activity. See Cravatt et al. *Proc. Natl. Acad. Sci. U.S.A.* 98:9371-9376 (2001).

Pharmaceutical Compositions

The invention also provides pharmaceutical compositions of the above peripherally restricted FAAH inhibitory compounds. The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. The term "pharmaceutical composition" indicates a composition suitable for pharmaceutical use in a subject, including an animal or human. A pharmaceutical composition generally comprises an effective amount of an active agent and a pharmaceutically acceptable carrier.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend in part on the nature and severity of the conditions being treated and on the nature of the active ingredient. An exemplary route of administration is the oral route. The compositions may be conveniently presented in unit dosage form and prepared by any of the methods well-known in the art of pharmacy.

In practical use, the compounds of the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations can contain at least 0.1 percent of active compound. The percentage of active compound in these compositions may, of course, be varied and may conveniently be between about 2 percent to about 60 percent of the weight of the unit. The amount of active compound in such therapeutically useful compositions is such that a therapeutically effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor. To prevent breakdown during transit through the upper portion of the GI tract, the composition may be an enteric coated formulation.

With respect to formulations with respect to any variety of routes of administration, methods and formulations for the administration of drugs are disclosed in Remington's Pharmaceutical Sciences, 17th Edition, (Gennaro et al. Eds., Mack Publishing Co., 1985). Remington's Pharmaceutical Sciences, Gennaro A R ed. 20th edition, 2000: Williams & Wilkins Pa., USA.

Administration

The compounds of the invention may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The compounds of the invention can be effective over a wide dosage range. For example, in the treatment of adult humans, dosages from about 10 to about 1000 mg, about 100 to about 500 mg or about 1 to about 100 mg may be needed. Doses of the 0.05 to about 100 mg, and more preferably from about 0.1 to about 100 mg, per day may be used. A most preferable dosage is about 0.1 mg to about 70 mg per day. In choosing a regimen for patients, it may frequently be necessary to begin with a dosage of from about 2 to about 70 mg per day and when the condition is under control to reduce the dosage as low as from about 0.1 to about 10 mg per day. For example, in the treatment of adult humans, dosages from about 0.05 to about 100 mg, preferably from about 0.1 to about 100 mg, per day may be used. The exact dosage will depend upon the mode of administration, on the therapy desired, form in which administered, the subject to be treated and the body weight of the subject to be treated, and the preference and experience of the physician or veterinarian in charge.

Generally, the compounds of the present invention can be dispensed in unit dosage form comprising preferably from about 0.1 to about 100 mg of active ingredient together with a pharmaceutically acceptable carrier per unit dosage. Usually, dosage forms suitable for oral, nasal, pulmonary or transdermal administration comprise from about 0.001 mg to about 100 mg, preferably from about 0.01 mg to about 50 mg of the compounds admixed with a pharmaceutically acceptable carrier or diluent. For storage and use, these preparations preferably contain a preservative to prevent the growth of microorganisms.

Administration of an appropriate amount the candidate compound may be by any means known in the art such as, for example, oral or rectal, parenteral, intraperitoneal, intravenous, subcutaneous, subdermal, intranasal, or intramuscular. In some embodiments, administration is transdermal. An appropriate amount or dose of the candidate compound may be determined empirically as is known in the art. An appropriate or therapeutic amount is an amount sufficient to provided the desired therapeutic effect (e.g., treat or alleviate pain or treat or reduce inflammation). The candidate compound can be administered as often as required to alleviate the pain or reduce the inflammation, for example, hourly, every six, eight, twelve, or eighteen hours, daily, or weekly Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Injection solutions and suspensions can be prepared from sterile powders, granules, and tablets of the kind previously described. Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

With respect to transdermal routes of administration, methods for transdermal administration of drugs are disclosed in Remington's Pharmaceutical Sciences, Gennaro A R ed. 20th edition, 2000: Williams & Wilkins PA, USA. Dermal or skin patches are a preferred means for transdermal delivery of the compounds of the invention. Patches preferably provide an absorption enhancer such as DMSO to increase the absorption of the compounds. Other methods for transdermal drug delivery are disclosed in U.S. Pat. Nos. 5,962,012, 6,261,595, and 6,261,595. Each of which is incorporated by reference in its entirety.

Preferred patches include those that control the rate of drug delivery to the skin. Patches may provide a variety of dosing systems including a reservoir system or a monolithic system, respectively. The reservoir design may, for example, have four layers: the adhesive layer that directly contacts the skin, the control membrane, which controls the diffusion of drug molecules, the reservoir of drug molecules, and a water-resistant backing.

Such a design delivers uniform amounts of the drug over a specified time period, the rate of delivery has to be less than the saturation limit of different types of skin.

The monolithic design, for example, typically has only three layers: the adhesive layer, a polymer matrix containing the compound, and a water-proof backing. This design brings a saturating amount of drug to the skin. Thereby, delivery is controlled by the skin. As the drug amount decreases in the patch to below the saturating level, the delivery rate falls.

Compounds of the invention may be used in combination with other compounds of the invention or with other drugs that may also be useful in the treatment, prevention, suppression of pain, inflammation, or immune disorders. In one embodiment, the second drug is not a FAAH inhibitor and is directed toward the same disorder as the FAAH inhibitor. Such other drugs may be administered, by a route and in an amount commonly used therefor, contemporaneously or sequentially with a compound of the invention. When a compound of the invention is used contemporaneously with one or more other drugs, a pharmaceutical composition in unit dosage form containing such other drugs and the compound is preferred. When used in combination with one or more other active ingredients, the compound of the present invention and the other active ingredients may be used in lower doses than when each is used singly. Accordingly, the pharmaceutical compositions of the present invention include those that contain one or more other active ingredients, in addition to the compounds disclosed above.

In the pharmaceutical compositions of the present invention for oral, sublingual, subcutaneous, intramuscular, intravenous, transdermal, local or rectal administration, the active principle, by itself or in association with another active principle, can be administered to animals and humans in unit forms of administration mixed with conventional pharmaceutical carriers. The appropriate unit forms of administration include oral forms such as tablets, gelatin capsules, powders, granules and solutions or suspensions to be taken orally, sublingual and buccal forms of administration, aerosols, implants, subcutaneous, intramuscular, intravenous, intranasal or intraocular forms of administration and rectal forms of administration.

In other embodiments, the pharmaceutical compositions of the present invention, the active principle or active principles are generally formulated in dosage units. The dosage unit contains from 0.5 to 1000 mg, advantageously from 1 to 500 mg and preferably from 2 to 200 mg of FAAH inhibitor per dosage unit for daily administration.

Methods of Treatment
Control of Pain

In some embodiments, the compounds of Formula I and II may be administered to alleviate or treat pain in a subject. The treatment may be prophylactic or therapeutic. The treatment may be administered to a human subject. The compounds and compositions of the invention may be administered solely for the purposes of reducing the severity or frequency or extent of pain. The treatment may be administered in a combination therapy with another pain reliever or anti-inflammatory agent. In some embodiments, the pain can be a neuropathic pain selected from the group consisting of post trigeminal neuralgia, neuropathic low back pain, peripheral or polyneuropathic pain, complex regional pain syndrome (causalgia and reflex sympathetic dystrophy), diabetic neuropathy, toxic neuropathy, and chronic neuropathy caused by chemotherapeutic agents. In other embodiments, the pain is renal and liver colic pain or fibromyalgia. In some neuropathic pain embodiments, the primary lesion or dysfunction of the nervous system is caused by a mechanical injury to a nerve of the subject. In a further embodiment, the mechanical injury is due to compression of a nerve, transection of nerve, causalgia, spinal cord injury, post surgical pain, phantom limb pain, or scar formation in the subject.

In other embodiments, the pain is a pain caused by inflammation or injury of a tissue. Inflammatory pain develops in response to tissue damage occurring from the noxious stimuli. In response to the tissue injury, cytokines and other mediators are released which strengthen nociception. As a result primary hyperalgesia (increased sensitivity to pain) occurring in the area of injury and a secondary hyperalgesia occurring in the tissue surrounding the injury ensue. The hyperalgesia subsides with the inflammation as the tissue is healed. In some further embodiments, the inflammation is associated with pulmonary edema, kidney stones, minor injuries, wound healing, skin wound healing, vaginitis, candidiasis, lumbar spondylanhrosis, lumbar spondylarthrosis, vascular diseases, migraine headaches, sinus headaches, tension headaches, dental pain, periarteritis nodosa, thyroiditis, aplastic anemia, Hodgkin's disease, sclerodoma, rheumatic fever, type I diabetes, type II diabetes, myasthenia gravis, multiple sclerosis, sarcoidosis, nephrotic syndrome, Behcet's syndrome, polymyositis, gingivitis, hypersensitivity, swelling occurring after injury, or myocardial ischemia, or osteoarthritis.

Control of Inflammation

In some embodiments, the compounds of Formula I and II may be administered to alleviate inflammation in a subject. The treatment may be prophylactic or therapeutic. The treatment may be administered to a human subject. The compounds and compositions of the invention may be administered solely for the purposes of reducing the severity or frequency or extent of the inflammation. The treatment may be administered in a combination therapy with another pain reliever or anti-inflammatory agent.

Control of Immune Disorders

The following examples are provided for illustrative purposes, and are not intended to limit the scope of the invention as claimed herein. Any variations in the exemplified articles and/or methods which occur to the skilled artisan are intended to fall within the scope of the present invention.

EXAMPLES

Materials and Methods

Drug distribution coefficients. We determined Log $D_{7.4,oct}$ values at room temperature (25±1° C.) partitioning the solutes between n-octanol and an aqueous solution buffered at pH 7.4[36].

Enzyme assays. We conducted standard FAAH and monoacylglycerol lipase assays as described[15,37], using as substrates [$^3$H]-anandamide (a gift of the National Institute on Drug Abuse) and 2-oleoyl-sn-glycerol (Nu-Check Prep, Elysian, Minn.), respectively.

Drug transport assays. Assays were performed at Cerep Inc. (Redmond, Wash.), following protocols outlined in the company's web-site (http://www.cerep.fr).

Tissue analyses. We performed tissue extractions and liquid chromatography/mass spectrometry analyses of endocannabinoids as described[38]. Similar procedures were utilized for the tissue extraction and LC/MS quantification of URB937, as detailed further below.

Fos expression. We measured Fos protein levels by quantitative immunocytochemistry[5] on slices of lumbar (L4/L5) spinal cord from male Sprague-Dawley rats.

Surgery. We performed sciatic nerve ligations in male Swiss mice, as previously described for rats[24] with minor modifications[39].

Behavioral tests. We measured nocifensive responses elicited by i.p. injection of acetic acid in male Swiss and C57B1/6 (wild-type or FAAH-deficient) mice[40], intraplantar injection of carrageenan in male Swiss mice[20], intraplantar injection of formalin in male Sprague-Dawley rats[41], and sciatic nerve ligation in male Swiss mice[39].

Synthesis of FAAH inhibitors URB937 was synthesized largely following a published procedure[36]. The compound was obtained in five steps starting from 3-bromo-4-hydroxybenzaldehyde, which was benzylated (BzCl, DMF, $CsCO_3$, rt, 3 h), then oxidized and hydrolyzed (m-CPBA, $CH_2Cl_2$, 40° C., 72 h; NaOMe, EtOH, rt, 1 h) to 4-benzyloxy-3-bromophenol; the latter was elaborated by Suzuki coupling [3-carbamoylphenylboronic acid, toluene, $Pd(PPh_3)_4$, $Na_2CO_3/H_2O$, reflux, 2 h], carbamation (c-$C_6H_{11}$CNO, $Et_3N$, toluene/$CH_3CN$ 1:1, reflux, 18 h) and hydrogenative deprotection to the desired compound. N-cyclohexyl-O-biphenyl-3-yl carbamates 1c-e were synthesized by reaction of the opportune 3'-carbamoyl-4-substituted phenol with cyclohexyl isocyanate, while 1f was obtained by a Pd/C catalyzed hydrogenation of the corresponding nitrocarbamate precursor, which results from the suitable phenol derivative. All biphenols were synthesized by a Suzuki cross-coupling reaction between 3-carbamoylphenylboronic acid and the corresponding 3-bromo-4-substituted phenols (in the case of the precursors of 1c,d) or 3-chloro-4-fluorophenol (for those of 1e). Detailed synthetic procedures for all the compounds will be reported elsewhere.

Synthesis of cyclohexylcarbamic acid 3'-carbamoyl-6-hydroxybiphenyl-3-yl ester (URB937). To a stirred suspension of cyclohexylcarbamic acid 3'-carbamoyl-6-benzyloxybiphenyl-3-yl ester (222 mg; 0.5 mmol) in EtOAc (2.5 mL) and EtOH (2.5 mL), 10% Pd/C (22 mg) was added. The mixture was hydrogenated at 4 atm at 50° C. for 4 h, cooled, filtered on Celite and concentrated. Purification of the residue by column chromatography (cyclohexane/EtOAc 1:9) and recrystallization gave URB937 as a white solid. Yield: 92% (0.163 g). Mp: 128-130° C. ($CH_2Cl_2$/n-hexane). MS (ESI) m/z: 355.2 (M+H). $^1$H NMR (200 MHz, $CDCl_3$) δ: =1.13-2.02 (m, 10H), 3.55 (m, 1H), 5.13 (br d, 1H), 5.85 (br s, 1H), 6.59 (br s, 1H), 6.74-6.95 (m, 3H), 7.07 (s, 1H), 7.34-7.41 (m, 1H), 7.56 (m, 1H), 7.68-7.75 (m, 2H) ppm. IR (Nujol) $n_{max}$: 3333, 1701, 1655 $cm^{-1}$.

Other chemicals [$^3$H]-Anandamide was purchased from American Radiolabeled Chemicals, Inc. (St. Louis, Mo.). 2-[$^2$H$_8$]-AG and AM630 were from Cayman Chemical (Ann Arbor, Mich.). Anandamide, [$^2$H$_4$]-anandamide and PEA were synthesized in the laboratory[42]. Rimonabant and N-cyclohexyl biphenyl-3-ylacetamide were kind gifts of the National Institute on Drug Abuse and Kadmus Pharmaceuticals Inc., respectively.

Animals We used male Swiss Webster mice (Charles River, 20-30 g), male C57B1/6 (Jackson Laboratory, 20-25 g), male FAAH-deficient mice (25-35 g) back crossed more than 10 times on a C57B1/6 background, male Wistar rats (Charles River, 250-300 g) and male Sprague-Dawley (SD) rats (Harlan Laboratories, 275-350 g). Mice and Wistar rats were group-housed in standard cages at room temperature on a 12:12 h light:dark cycle with unlimited access to water and standard chow pellets. Wistar rats were typically used for the FAAH studies. All experiments met the National Institutes of Health guidelines for the care and use of laboratory animals, were approved by the Institutional Animal Care and Use Committee of the University of California, Irvine, and the University of Georgia, Athens, and were in compliance with the European Community Council Directive 86 (609) EEC and the experimental protocol was carried out in compliance with Italian regulations (DL 116/92).

Tissue extractions Mice were sacrificed with isoflurane and tissues were collected and immediately frozen in liquid nitrogen. Frozen tissues were weighed and homogenized in methanol (1 mL) containing [$^2$H$_4$]-anandamide, [$^2$H$_4$]-PEA, [$^2$H$_8$]-2-AG, and N-cyclohexyl biphenyl-3-ylacetamide as internal standards. Analytes were extracted with chloroform (2 vol) and washed with water (1 vol). Organic phases were collected and dried under nitrogen. The non-fractionated organic extract was used for quantification of URB937. For other analyses the organic extract was fractionated by open-bed silica gel column chromatography, as described[43]. Briefly, the extract was dissolved in chloroform and loaded onto small glass columns packed with Silica Gel G (60~A 230-400 Mesh ASTM; Whatman, Clifton, N.J.). Anandamide, PEA and 2-AG were eluted with chloroform/methanol (9:1, vol/vol).

Serum extractions Trunk blood was collected from decapitated mice, allowed to clot and placed on ice. The clotted blood was centrifuged at 18,000×g for 10 min at 4° C. and the serum was transferred to glass vials and diluted with distilled water to 1 mL. Proteins were precipitated with ice-cold acetone (1 mL) containing N-cyclohexyl biphenyl-3-ylacetamide as an internal standard, and the precipitate was removed by centrifugation at 3000×g for 10 min at 4° C. The samples were dried under nitrogen to remove acetone, and extracted with chloroform/methanol as described above.

Liquid chromatography/mass spectrometry (LC/MS) Tissue levels of anandamide, PEA, 2-AG and URB937 were determined using an 1100-LC system coupled to a 1946A-MS detector (Agilent Technologies, Inc., Palo Alto, Calif.) equipped with an electrospray ionization interface. URB937 and N-cyclohexyl biphenyl-3-ylacetamide (m/z=294) were eluted on an XDB Eclipse $C_{18}$ column (50×4.6-mm inner diameter, 1.8 μm, Zorbax) using a linear gradient of 60% to 100% of A in B over 3 min at a flow rate of 1.0 mL-min$^{-1}$. Mobile phase A consisted of methanol containing 0.25% acetic acid, 5 mM ammonium acetate; mobile phase B consisted of water containing 0.25% acetic acid, 5 mM ammonium acetate. Anandamide, 2-AG and PEA were eluted with a gradient of methanol in water (from 85% to 90% methanol in 2.5 min) at a flow rate of 0 1.0 mL-min$^{-1}$. Column temperature was kept at 40° C. MS detection was in the positive ionization mode, capillary voltage was set at 3 kV, and fragmentor voltage was varied from 120 to 140 V. Nitrogen was used as drying gas at a flow rate of 13 L-min$^{-1}$ and a temperature of 350° C. Nebulizer pressure was set at 60 psi. Na$^+$ adducts ([M+Na$^+$]) of analytes and internal standards were monitored in the selective ion-monitoring mode. Limit of quantification was 0.4 pmol.

Drug transport assays Transport assays were conducted at Cerep Inc. (Redmond, Wash.). Cellular permeability was determined in the apical (A) to basal (B) and the B to A direction in the presence of 10 μM compound in Hanks' buffered salt solution containing 1% dimethylsulfoxide (DMSO). Efflux ratios were calculated as the ratio of B-A to A-B permeabilities.

Fos immunohistochemistry Two hours after formalin injection into the dorsal paw, rats received a lethal dose of Nembutal (50 mg-mL$^{-1}$). They were perfused through the heart with 100 mL of 1% heparinized phosphate buffered saline (PBS) followed by 300 mL of ice-cold 4% paraformaldehyde. The lumbar-sacral region of the spinal cord was collected from each rat. Spinal cords were post fixed in 4% paraformaldehyde at 4° C. for 24 h and then cryoprotected in 30% sucrose at 4° C. for 24-48 hours. Spinal cords were cryostat-cut into 40 μm transverse sections at the level of the lumbar enlargement (L4/L5). Free floating alternating sections were kept in a series of wells filled with PBS. Every fourth section was processed for Fos immunoreactivity to ensure that the same cell would not be counted twice. Endogenous peroxidases were inactivated by incubation in hydrogen peroxide. Sections were blocked with goat serum to prevent non-specific binding and were incubated in the presence of Fos primary antibody (1:20,000, Abcam, Cambridge, Mass., USA) diluted in PBS containing 0.4% Triton (for 1 h at 37° C. and then 48 h at 4° C.). Tissue was incubated in the presence of biotinylated goat anti-rabbit IgG (1:600, Vector Laboratories, Burlingame, Calif., USA) secondary antibody for 1 h at 37° C. Subsequently, sections were incubated in a Vectastain Elite ABC reagent (1:200, Vector Laboratories) for 1 h, followed by a 5 min incubation in 2% nickel intensified diaminobenzidine. Sections were mounted onto glass slides, air dried, dehydrated in ascending concentrations of ethanol, cleared in xylene, and protected by a glass coverslip affixed with Permount. All conditions in the same experiment were processed concurrently, to control for variance in immunostaining across different runs. Immunostaining specificity was established by primary antibody omission from the immunostaining protocol and by demonstration that preadsorbtion with the peptide antiserum blocked specific staining[5].

Immunoreactivity quantification Under a microscope, three L4 sections that qualitatively exhibited the greatest number of Fos-positive cells were selected for quantification. Selection of sections and quantification of the number of Fos-positive cells was performed by an observer blinded to experimental conditions. Sections were captured at 5× magnification using a DMLB light microscope and a 1,300 digital camera under similar brightness/contrast settings to demonstrate comparable background staining Laminar subdivisions were drawn on all sections using the Image J software (U.S. National Institutes of Health, Bethesda, Md., USA). Subdivisions of the spinal gray matter were defined as the superficial laminae (laminae I and II), nucleus proprius (laminae III and IV), neck of the dorsal horn (laminae V and VI), and ventral horn (laminae, VII, VIII, IX, and X)[44]. Using Image J, Fos expressing cells were counted in each subdivision, regardless of staining intensity, by an observer blinded to experimental treatments. The intra-rater reliability ranged from 93% in the superficial lamina to 81% across all lamina subdivisions.

Drug preparation for in vivo experiments Drugs were dissolved in polyethylene glycol 400/Tween-80/saline (1/1/18; by volume) and administered by i.p. (5-10 mL-kg$^{-1}$) or s.c. injection (10 mL-kg$^{-1}$). For lateral cerebral ventricle injections, URB937 was dissolved in 100% DMSO and injected in a volume of 5 μL.

Surgeries All surgeries were conducted under aseptic conditions. Implantation of cannulae for intracerebroventricular (i.c.v.) drug administration. SD rats were anesthesized using a mixture of ketamine (70 mg-kg$^{-1}$, i.p.) and xylazine (9.33 mg-kg$^{-1}$, i.p.). They were placed in a stereotaxic frame and stabilized by ear bars (David Kopf Instruments, Tujunga, Calif., USA) with the incisor bar set 2.4 mm below the horizontal plane. A 22-gauge stainless-steel guide cannula was implanted into the right lateral cerebral ventricle 7 days prior to experiments. Coordinates for implantation (−0.9 mm antero/posterior and −1.5 mm medio/lateral relative to bregma, and 3.8 mm below the surface of the skull) were determined using the Paxinos and Watson rat brain atlas[45]. Guide cannulae were anchored to the skull with 3 stainless-steel screws and dental cement, and were kept patent until injection by insertion of a dummy stylet. For injections, the stylet was removed and drug or vehicle were infused in a volume of 5 μL with a 10 μL Hamilton microsyringe connected to a 28 gauge stainless-steel injector, which protruded 1 mm beyond the tip of the guide cannula, by a PTFE 24G catheter (Small parts Inc, Logansport, Ind.) filled with PBS. A small air bubble (3 μL) was drawn at the distal end of the PTFE 24G catheter to separate the injected solution from the PBS and for visual inspection of the injection. Injections were performed over a 1-min period and the injector was kept in place for an additional 1 min to prevent back flow leakage. Placement of the cannula was verified at the end of the experiments by injection of trypan blue (5 μL) before the rats were euthanized. Only animals with proper placements were included in the study. Rats were allowed to recover for 7-10 days before experiments. Sciatic nerve ligation was performed in Swiss mice, using an adaptation of the method of Bennett and Xie[24]. Mice were anesthetized with xylazine (10 mg-kg$^{-1}$, i.p.) and ketamine (100 mg-kg$^{-1}$, i.p.), the left thigh was shaved and scrubbed with Betadine®, and a small incision (2 cm in length) was made in the middle of the left thigh to expose the sciatic nerve. The nerve was loosely tied at two distinct sites (spaced at a 2-mm interval) around the entire diameter of the nerve using silk sutures (7-0). The surgical area was dusted with streptomycin powder and closed with a single muscle suture and two skin clips and finally scrubbed with Betadine®. In sham-operated animals, the nerve was exposed but left untied. The animals were placed under a heat lamp until they awakened.

Behavioral tests Acetic acid-induced writhing was measured in Swiss mice or C57B1/6 mice (wild-type and FAAH-deficient), as described[40] with minor modifications. Briefly, the mice were acclimated to the experimental room for 2 h. Each animal was injected with acetic acid (150 μL, 0.6% in saline) and placed into a glass cylinder. Abdominal stretches (extension of body and hind limbs) were counted for 20 min, starting 5 min after acetic acid injection. URB937, rimonabant and AM630 were administered by s.c. injection 1 h before acetic acid. Behavior was scored by an observer blinded to the treatment conditions. Formalin-induced nociception was assessed in Sprague-Dawley rats, as described[41]. The rats were singly housed and kept in a shared holding room under a 12:12 h light:dark cycle. They were given free access to food and water, and allowed to acclimate to the facility for a week before testing. One h prior to formalin administration, the rats received i.p. injections of vehicle, URB937 (1 mg-kg$^{-1}$, i.p.), rimonabant (2 mg-kg$^{-1}$ i.p.) or a combination of URB937 and rimonabant. They were acclimated to the observation container (clear plexiglas box, 29×29×25 cm) for 15 min before receiving an injection of formalin (50 μL, 5% in saline) into the dorsal surface of the right hind paw. Immediately after formalin injection, the rats were returned to the observation container and nocifensive behavior was recorded for 60 min with a video camera. Recordings were analyzed by observers blinded to treatment conditions. Nocifensive behavior was measured continuously for 60 min[41]. The total time spent by the animals in three different behavioural categories (0, 1, 2) was recorded in 5-min bins where: (0) the rat exhibits normal posture, (1) the injected paw is raised, or (2) the injected paw is licked, shaken or bitten. Each 5-min bin was analyzed for time spent (1) lifting and (2) licking or biting the injected paw. Nocifensive behavior was analyzed using the composite pain score weighted scores technique (CPS-WST1,2) calculated for the entire time of observation (0-60 min) and, separately, for the first (0-10 min) and second phase (10-60 min) of the behavioral response[46]. The area under the curve (AUC) corresponding to CPS-WST1,2 was calculated using the trapezoidal rule. Paw edema was induced in mice by injection into the right hind paws of 50 μL of sterile saline containing 1% λ-carrageenan. Paw volumes were measured using a plethysmometer (Ugo Basile, Milan, Italy). Vehicle or URB937 (1 mg kg$^{-1}$, i.p.) were injected immediately before carrageenan. Rimonabant and AM630 (1 mg kg$^{-1}$, i.p.) were injected 30 min before carrageenan. Mechanical hyperalgesia was assessed by measuring the latency(s) to withdraw the paw from a constant mechanical pressure exerted onto its dorsal surface. A 15-g calibrated glass cylindrical rod (diameter=10 mm) chamfered to a conical point (diameter=3 mm) was used to exert the mechanical force. The weight was suspended vertically between two rings attached to a stand and was free to move vertically. A cutoff time of 3 min was used. Thermal hyperalgesia was assessed as described[47], measuring the latency to withdraw the hind paw from a focused beam of radiant heat (thermal intensity: infrared 3.0) applied to the plantar surface, using a commercial apparatus (Ugo Basile, Varese, Italy). The cutoff time was set at 30 s. Mechanical allodynia was assessed by applying a graded force to the plantar hind paw surface with a Von Frey filament, using a Dynamic Plantar Anesthesiometer (Ugo Basile). The cutoff force was set at 50 g.

Statistical Analyses Results are expressed as the mean±s.e.m. Statistical significance was determined by Students t test, one-way, or two-way analysis of variance (ANOVA) followed by Bonferroni post hoc test when appropriate. A separate univariate analysis of variance was performed to determine the effects of experimental treatment on formalin-induced nocifensive behavior as measured by area under the curve. A repeated measures (Treatment×Time [repeated factor]) analysis of variance was performed on formalin-induced composite pain score. The Greenhouse-Geisser correction was applied to all repeated factors. For each laminar subdivision at L4/L5 of the spinal cord, a univariate analysis of variance was performed to determine the effects of experimental treatment on the number of Fos-expressing cells. Fisher's LSD and Tukey post hoc tests were performed on behavioral and Fos immunostaining data, respectively. Post hoc comparisons that did not meet the equal variance assumption were corrected by fractional adjustment of the degrees of freedom. Analyses were performed using SPSS statistical software (version 17.0; SPSS Incorporated, Chicago, Ill., USA).

Results

Figure 1B:
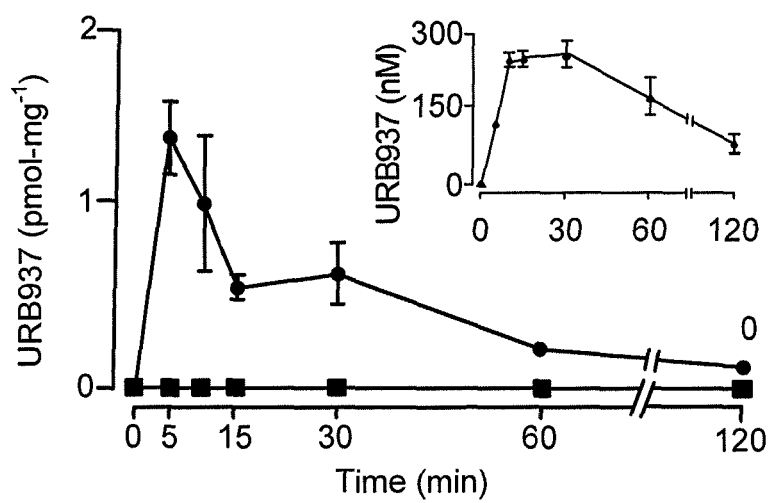
Figure 1C:
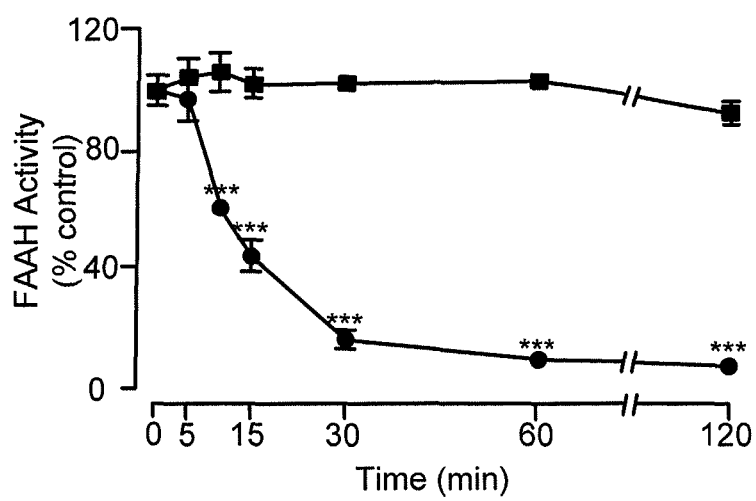

Discovery of a peripherally restricted FAAH inhibitor Current FAAH inhibitors readily cross the blood-brain barrier[12]. To produce inhibitors with restricted access to the CNS, we added chemical groups of varying polarity to the proximal phenyl ring of the O-arylcarbamate URB597[13,14] (Table 1, 1a), in a position where small-sized hydrophilic substituents are not expected to impair biological activity[15]. The new compounds had comparable potencies when tested in membrane preparations of rat brain FAAH, and were equally effective at blocking liver FAAH activity when administered systemically in mice (1 mg-kg$^{-1}$, intraperitoneal, i.p.) (Table 1, 1b-1f). They markedly differed, however, in their ability to access the CNS. In particular, the p-hydroxyphenyl derivative URB937 (Table 1, 1b) suppressed FAAH activity in peripheral tissues of mice and rats, yet failed to affect brain FAAH activity (Table 1, Table 2). A dose-exploration study in mice showed that the median effective dose ($ED_{50}$) of URB937 for FAAH inhibition in brain was 200 times higher than the $ED_{50}$ for FAAH inhibition in liver (FIG. 1a). Moreover, after systemic administration, URB937 (1 mg-kg$^{-1}$, i.p.) distributed rapidly in serum and liver, but remained undetectable in brain tissue (FIG. 1b). As seen with other O-arylcarbamates, which are known to interact with FAAH through a covalent mechanism[13,16], URB937 inhibited peripheral FAAH activity in vivo both rapidly and lastingly (FIG. 1c).

Mechanism of peripheral segregation Exploratory structure-activity relationship analyses indicate that the polarity of the p-hydroxyphenyl moiety is an essential contributor to the peripheral segregation of URB937. Table 1 shows that analogs in which the R substituent was weakly polar or apolar— compounds 1c, 1d and 1e—readily entered the brain after systemic administration in mice, whereas an analog in which R consisted of a polar amino group, compound 1f, was largely excluded. Nevertheless, the relatively high lipophilicity of URB937 (distribution coefficient, Log $D_{oct,pH7.4}$: URB937, 3.03±0.01; URB597, 3.71±0.01; mean±sem, n=3) should permit the passive diffusion of the molecule into the CNS unless this process is actively countered. As a first test of this idea, we determined the permeability and efflux ratios of URB937 through polarized monolayers of human epithelial TC7 cells, which express various protein transporters involved in the extrusion of drugs from the brain[17]. URB937 did not equally distribute across the apical (A) and basal (B) compartments of TC7 monolayers, as would be expected of a lipophilic molecule moving by passive diffusion. Rather, the compound accumulated into the A compartment [permeability, in nm-s$^{-1}$ (% recovery) A-B, 38 (83%); B-A, 371 (95%); efflux ratio, 9.8; mean of 2 independent experiments], through a mechanism that was insensitive to the permeability-glycoprotein (Pgp) inhibitor verapamil (100 µM) [B-A permeability in nm-s$^{-1}$ (% recovery): 322 (94%)]. These findings suggest that URB937 is extruded from the CNS by a transport system that is pharmacologically distinct from Pgp. Consistent with this interpretation, injection of a sub-maximal dose of URB937 (0.1 mg-kg$^{-1}$) into the lateral cerebral ventricles of rats produced within 1 h an almost complete inhibition of liver FAAH (residual activity: 11.3±1.9% of control; mean±sem, n=3). Conversely, systemic administration of a 10 times higher dose of drug (1 mg-kg$^{-1}$, i.p.) had no detectable effect on rat brain FAAH (Table 2).

To investigate the identity of the transport system involved in the extrusion of URB937 from the CNS, we administered in rats various pharmacological inhibitors of blood-brain barrier transporters along with the highest system dose of URB937 that does not achieve brain penetration (25 mg-kg$^{-1}$, i.p.)(FIG. 1a). Co-administration of the compound Ko-143, an inhibitor of breast cancer resistance protein (BCRP, ABCG1) caused a dose-dependent increase in the access of URB937 to the brain. By contrast, co-administration of verapamil, a permeability-glycoprotein (Pgp) inhibitor, or probenecid, an organic anion transport protein inhibitor, had no such effect. The results suggest that URB937 is extruded from the CNS by a transporter protein that is pharmacologically indistinguishable from BCRP.

Figure 1D:
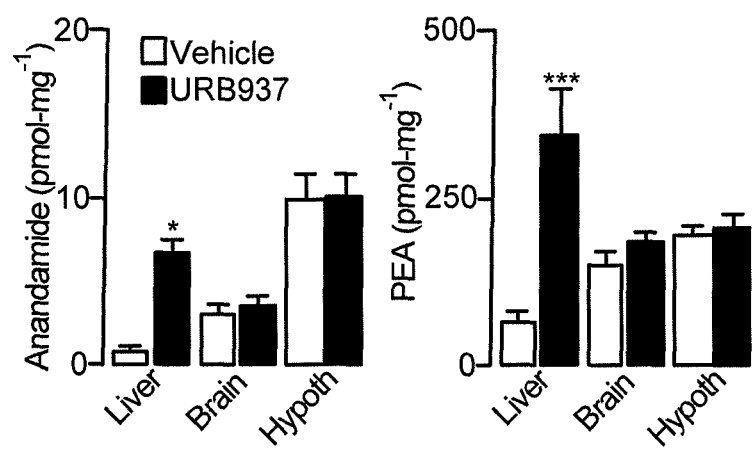
Figure 1E:
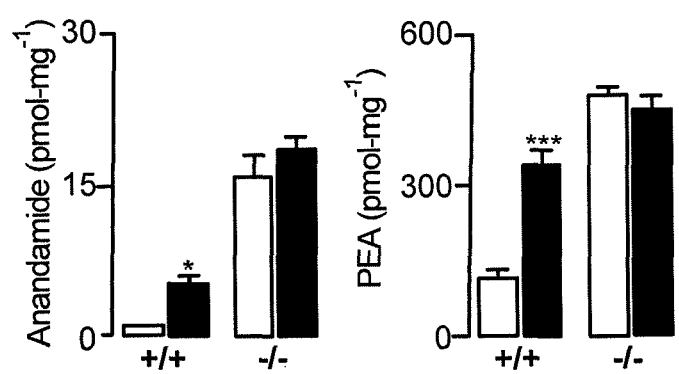
Figure 1F:
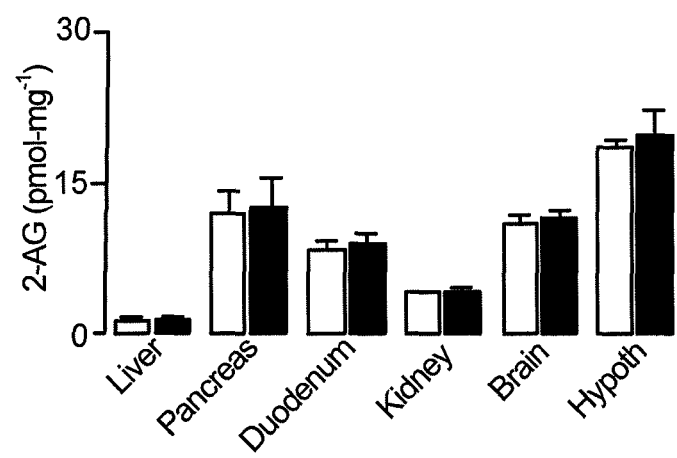
Figure 6:
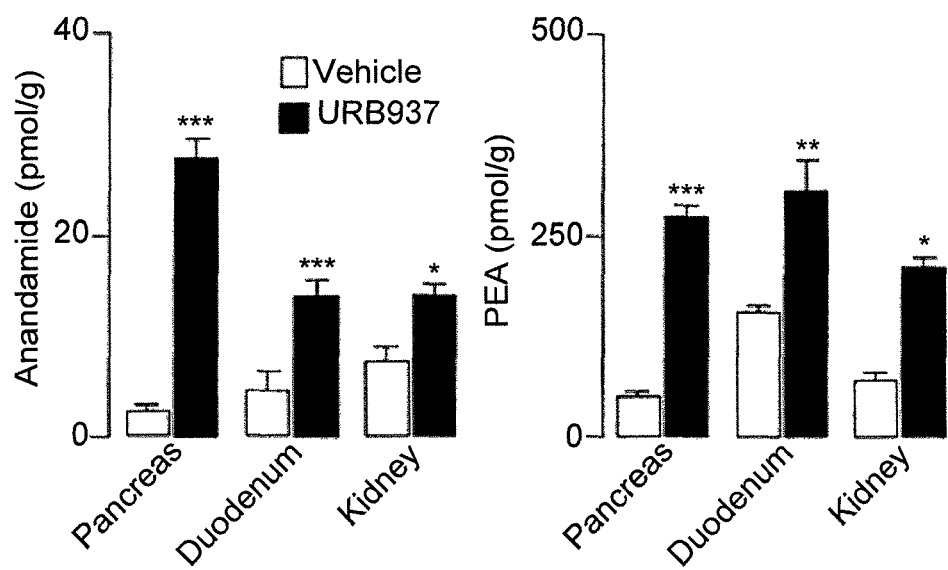
FIG. 6 Effects of URB937 (1 mg-kg$^{-1}$, i.p.) on anandamide and palmitoylethanolamide (PEA) levels in tissues of Swiss mice. Open bars, vehicle; closed bars, URB937. Results are expressed as mean±s.e.m., n=4-6. *, $P<0.05$, , $P<0.01$, *, $P<0.001$ vs vehicle.

Enhancement of peripheral anandamide signaling Administration of URB937 (1 mg-kg$^{-1}$, i.p.) in mice increased anandamide levels in the periphery, not in forebrain or hypothalamus (FIG. 1d, FIG. 6). This effect was caused by selective inhibition of FAAH activity because (i) it was accompanied by elevations in other endogenous FAAH substrates, such as palmitoylethanolamide (PEA) (FGI. 1d); and (ii) it was not observed in mutant mice in which expression of the faah gene had been disrupted by homologous recombination[18] (FIG. 1e). Importantly, URB937 did not affect monoacylglycerol lipase activity in vitro (median inhibitory concentration, $IC_{50}$, >100 µM; n=3) and did not alter tissue levels of its endocannabinoid substrate, 2-AG, in vivo (FIG. 1f).

Figure 2A:
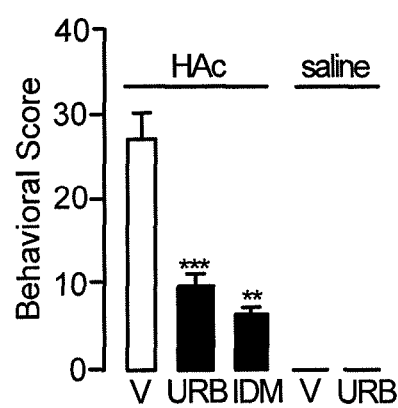
FIG. 2 URB937 inhibits behavioral responses to noxious chemicals in mice and rats. (a-d) Acetic acid (HAc)-induced pain behavior in mice. (a) Pain behavior (number of writhing episodes) assessed 1 h after administration of vehicle (V), URB937 (URB, 1 mg-kg$^{-1}$, i.p.) or indomethacin (IDM, 1 mg-kg$^{-1}$, i.p.). Also illustrated are the effects of vehicle and URB937 administered without acetic acid. (b) Statistical correlation between antinociception and inhibition of liver FAAH activity elicited by URB937 (1 mg-kg$^{-1}$, i.p.). (c) Effects of URB937 (1 mg-kg$^{-1}$, i.p.) on acetic acid-induced writhing in wild-type C57Bl/6 mice (+/+) and FAAH-deficient mice (−/−). (d) $CB_1$ antagonist rimonabant (Rim, 1 mg-kg$^{-1}$, s.c.), but not $CB_2$ antagonist AM630 (1 mg-kg$^{-1}$, s.c.), prevents the antinociceptive effects of URB937. Results are expressed as mean±s.e.m.; n=5-17. *P<0.05 vs vehicle; P<0.01 vs vehicle; and *P<0.001 vs vehicle; [##]P<0.01 vs URB937; [####]P<0.001 vs URB937. (e-g) Formalin-induced pain behavior in rats. (e) URB937 (1 mg-kg$^{-1}$, i.p.) produced time-dependent changes in composite pain score relative to vehicle, rimonabant (2 mg-kg$^{-1}$, i.p.) or a combination of URB937 and rimonabant ($F_{14,22}$=1.86, P=0.039). Formalin was injected at time=0. (f) URB937 (1 mg-kg$^{-1}$, i.p.) decreased the area under the curve (AUC) of pain behavior during the entire formalin response ($F_{3,22}$=3.32, P=0.039). (g) The antinociceptive effect of URB937 was limited to Phase 2 of the formalin response (10-60 min; $F_{1,3}$=3.05, P=0.050) whereas pain behavior during Phase 1 (0-10 min) was not reliably altered ($F_{1,3}$=2.22, P=0.115). Results are expressed as mean±s.e.m.; n=5-7. *P<0.05, all groups vs URB937; [#]P<0.05, URB937 or URB937 plus rimonabant vs vehicle.
Figure 2B:
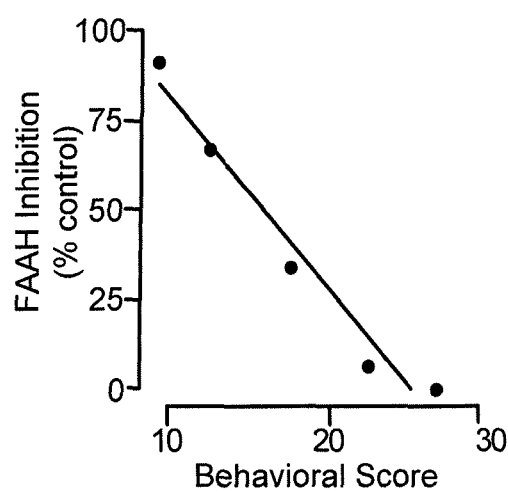
Figure 2C:
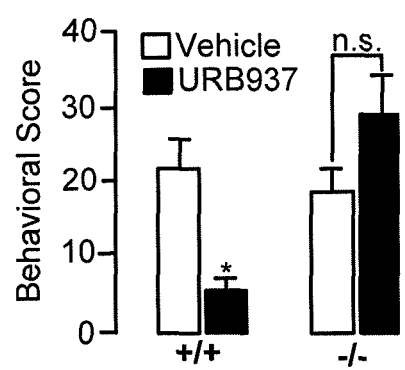
Figure 2D:
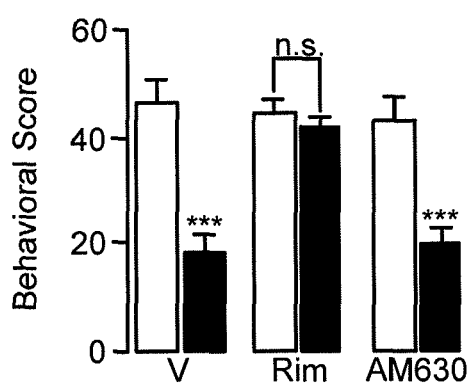

Modulation of visceral pain Brain-penetrating FAAH inhibitors attenuate behavioral responses to noxious stimuli in rodents, a property that is generally attributed to their ability to augment anandamide signaling in the brain and spinal cord[12,13]. To test whether peripheral anandamide contributes to these actions, we examined the effects of URB937 on the nocifensive (pain-avoiding) response evoked by injection of acetic acid into the peritoneal cavity of mice. Subcutaneous administration of URB937 reduced acetic acid-induced writhing with an $ED_{50}$ of 0.1 mg-kg$^{-1}$ (FIG. 2a and data not shown). This effect was (i) comparable in efficacy to that elicited by the potent non-steroidal analgesic indomethacin (1 mg-kg$^{-1}$, s.c.) (FIG. 2a); (ii) correlated with the degree of peripheral FAAH inhibition (Pearson correlation coefficient, r=0.96, FIG. 2b); and (iii) absent in mutant FAAH-deficient mice (FIG. 2c). The antinociceptive effects of URB937 were blocked by the $CB_1$ antagonist rimonabant, but not by the $CB_2$ antagonist AM630 (each at 1 mg-kg$^{-1}$, s.c.) (FIG. 2d).

Although anandamide is an agonist of vanilloid type-1 transient receptor potential (TRPV-1) channels[19], URB937 evoked no detectable nocifensive behavior when administered alone (1 mg-kg$^{-1}$) (FIG. 2a), which suggests that the tissue concentrations reached by endogenous anandamide following peripheral FAAH inhibition are unable to activate TRPV-1 channels. Moreover, stimulation of type-a peroxisome proliferator-activated receptors, which can be induced by PEA[20,21] (FIG. 1d), is unlikely to explain the antinociceptive effects of URB937 because such effects were prevented by $CB_1$ receptor blockade (FIG. 2d).

Figure 2E:
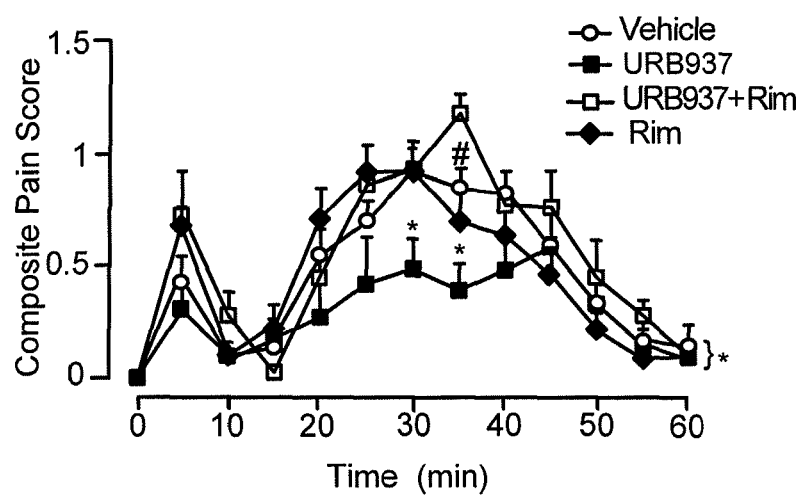
Figure 2F:
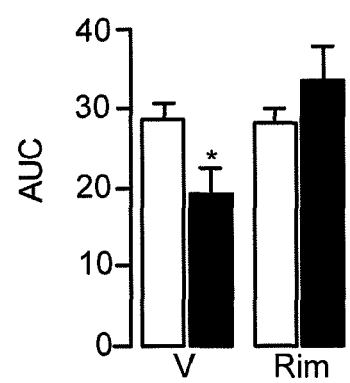
Figure 2G:
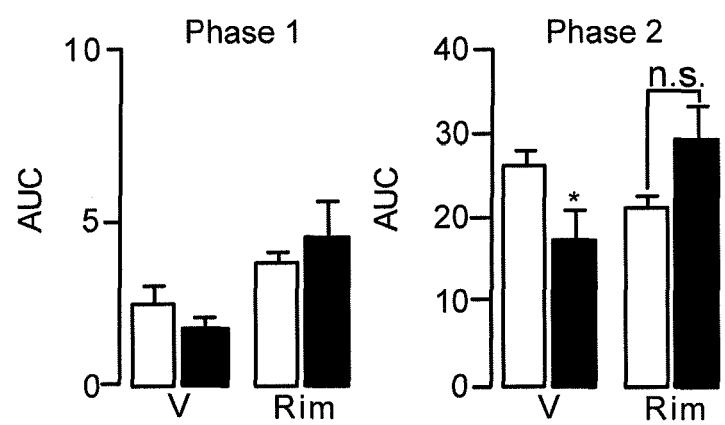

Modulation of tissue injury-induced pain In another series of experiments, we assessed the impact of URB937 (1 mg-kg$^{-1}$, i.p.) in a tissue injury model of persistent pain produced by administration of formalin into the dorsal hind paw of rats. Formalin injection elicited a marked nocifensive response, which was attenuated in a time-dependent manner by URB937, when compared to vehicle, rimonabant (2 mg-kg$^{-1}$, i.p.), or a combination of rimonabant and URB937 (FIG. 2e). Further analyses revealed that (i) URB937 decreased the area under the curve of formalin-induced pain behavior, relative to all other treatment groups (FIG. 2f); and (ii) this effect was primarily due to a reduction in the late phase (Phase 2) of the formalin response (FIG. 2g), in which ongoing primary afferent fiber activity is accompanied by inflammation and central sensitization of spinal nociceptive circuits[22,23].

Figure 3:
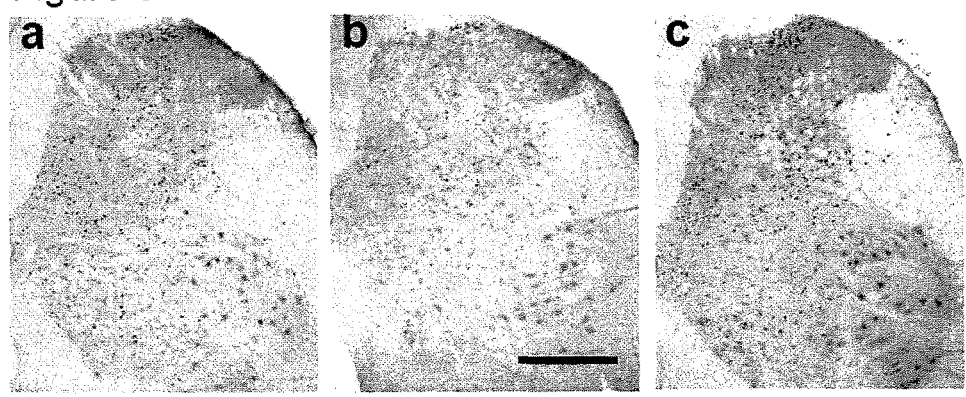
FIG. 3 URB937 suppresses formalin-induced Fos protein expression in rat lumbar (L4) spinal cord. (a-c) Representative sections showing formalin-induced Fos-positive cells in lumbar segments after injection of (a) vehicle; (b) URB937 (1 mg-kg$^{-1}$, i.p.); or (c) URB937 plus rimonabant (2 mg-kg$^{-1}$, i.p.). Calibration bar, 1 mm. (d) Quantitative analysis of the effects of vehicle (open bars), URB937 (closed bars), rimonabant, and URB937 plus rimonabant on number of Fos-positive cells in superficial dorsal horn (lamina I, II), nucleus proprius (lamina III, IV), neck region of the dorsal horn (lamina V, VI), and ventral horn. Behavioral data from the same subjects are shown in FIG. 2. Results are expressed as mean±s.e.m.; n=5-7. *$P<0.05$, all groups vs URB937; #$P<0.05$, URB937 plus rimonabant, or rimonabant alone vs URB937; &$P<0.05$, vehicle, rimonabant vs URB937.
Figure 3D:
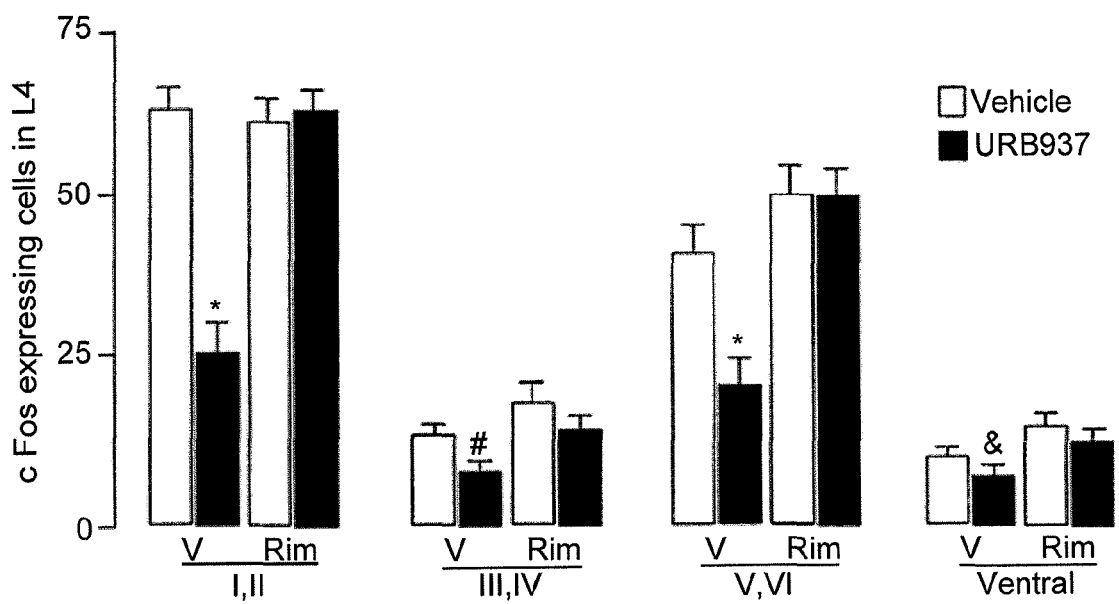

To determine whether enhancement of peripheral anandamide activity alters the spinal processing of nociceptive inputs, we measured formalin-induced Fos expression in the same animals subjected to behavioral testing. URB937 lowered the Fos response to formalin (FIG. 3a,b), decreasing the number of Fos-positive cells in the superficial dorsal horn (lamina I, II), nucleus proprius (lamina III, IV), neck region of the dorsal horn (lamina V, VI), and ventral horn (FIG. 3d). This effect was prevented by the $CB_1$ antagonist rimonabant (2 mg-kg$^{-1}$, i.p.), which did not significantly alter Fos levels when administered without URB937 (FIG. 3c,d). The ability of URB937 to suppress spinal nociceptive processing, despite its lack of CNS penetration, suggests that peripheral anandamide modulates pain inputs before they enter the spinal cord.

Figure 4A:
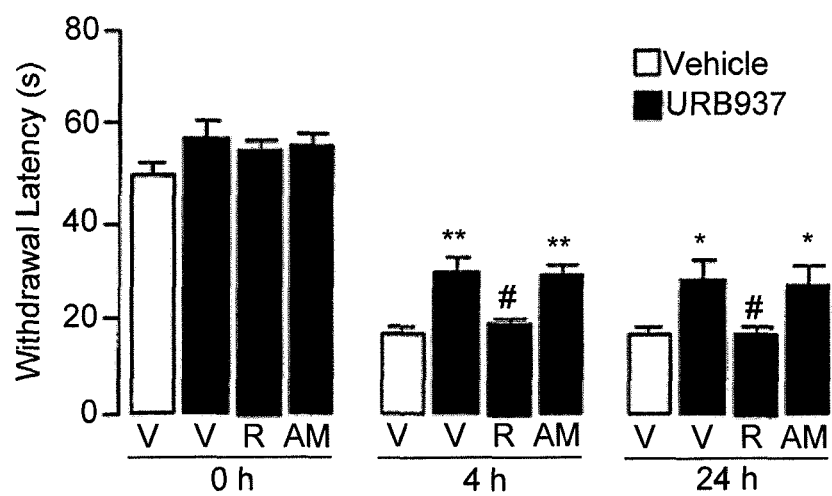
FIG. 4 URB937 attenuates pain behavior elicited by peripheral inflammation in mice. Effects of URB937 (1 mg-kg$^{-1}$, i.p.), administered alone or in combination with rimonabant (R, 1 mg-kg$^{-1}$, i.p.) or AM630 (AM, 1 mg-kg$^{-1}$, i.p.), on (a) carrageenan-induced mechanical hyperalgesia; (b) thermal hyperalgesia; (c) mechanical allodynia; and (d) paw edema. Mechanical and thermal hyperalgesia were measured immediately before carrageenan injection (0 h) or at 4 h and 24 h after injection. Mechanical allodynia was measured 0 h and 24 h after carrageenan. Results are expressed as mean±s.e.m.; n=6. *$P<0.05$ vs vehicle; $P<0.01$ vs vehicle; *$P<0.001$ vs vehicle; #$P<0.05$ vs URB937; ###$P<0.01$ vs URB937.
Figure 4B:
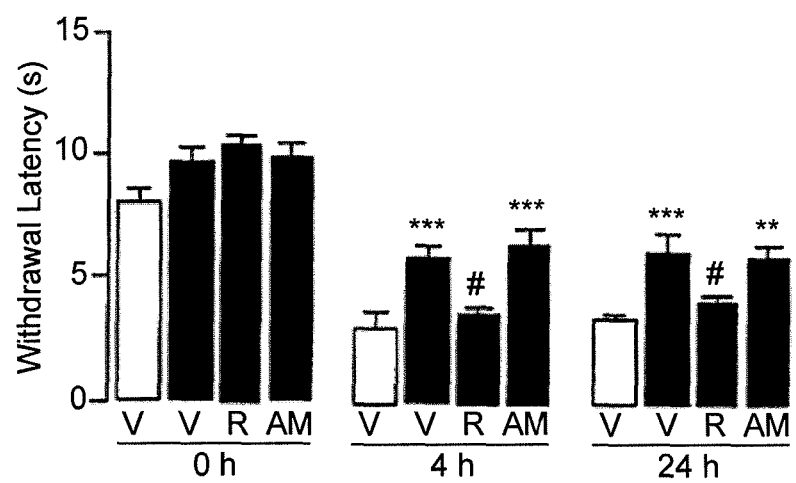
Figure 4C:
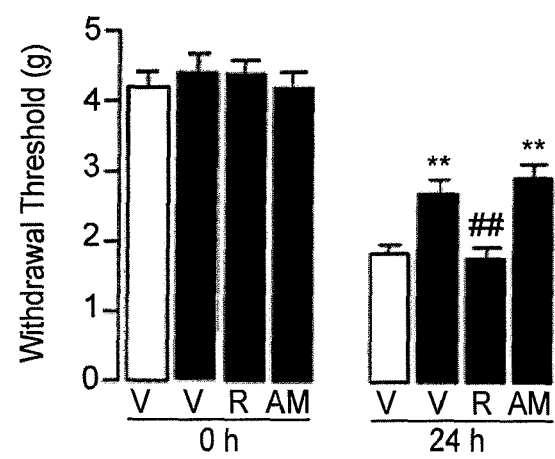
Figure 4D:
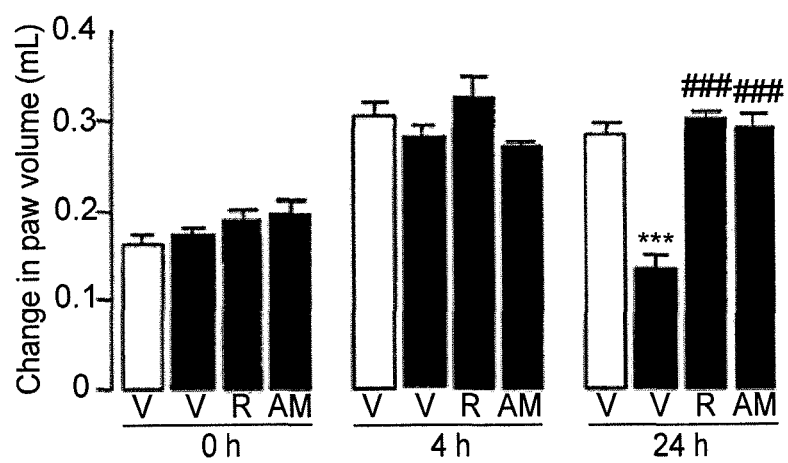
Figure 7A:
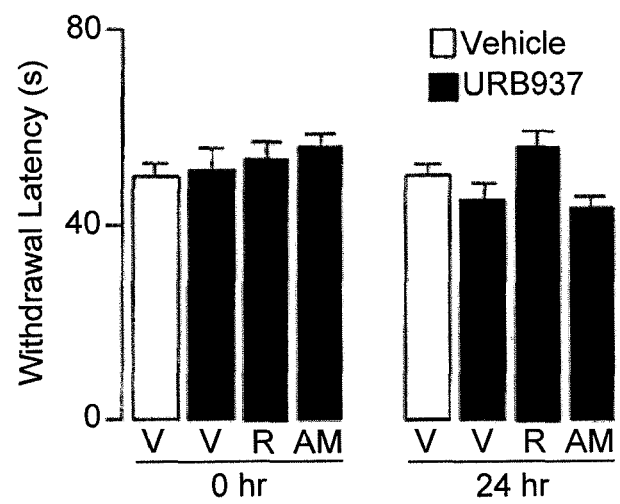
FIG. 7 Intraplantar injection of carrageenan does not affect mechanical (a) and thermal hyperalgesia (b) or mechanical allodynia (c) in contralateral (non-injected) paws of Swiss mice. Rimonabant (R, 1 mg-kg$^{-1}$, i.p.) and AM630 (1 mg-kg$^{-1}$, i.p.) had no effect. Results are expressed as mean±s.e.m.
Figure 7B:
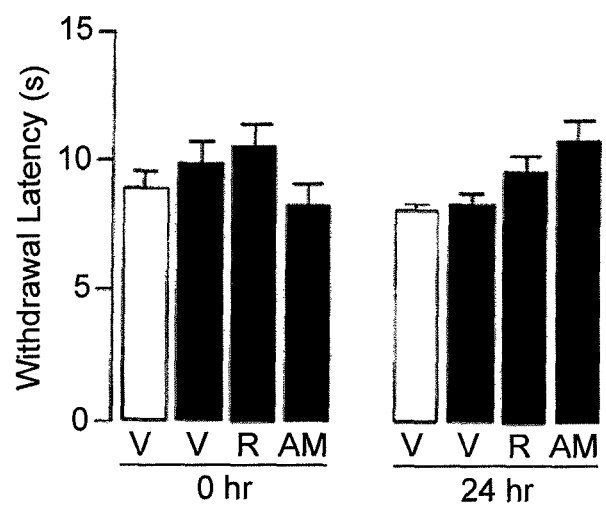
Figure 7C:
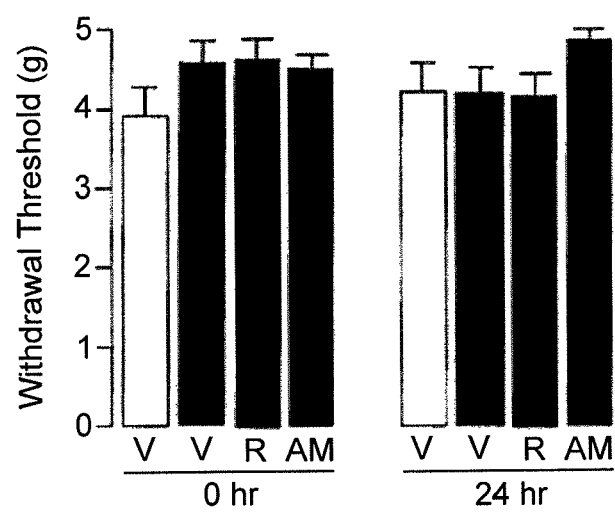

Modulation of inflammatory and neuropathic pain We also asked whether peripheral inhibition of FAAH activity might influence persistent pain responses caused by inflammation or nerve damage. We induced an inflammatory reaction in mice by injecting the polysaccharide carrageenan into one of their hind paws. This resulted in the development of mechanical and thermal hyperalgesia (heightened sensitivity to noxious stimuli) as well as local edema (FIG. 4). A single systemic injection of URB937 (1 mg-kg$^{-1}$, i.p.), administered at the same time as carrageenan, caused a significant decrease in mechanical and thermal hyperalgesia, assessed 4 h and 24 h following carrageenan treatment (FIG. 4a,b). The drug also suppressed mechanical allodynia (pain from non-noxious stimuli) measured 24 h after carrageenan (FIG. 4c). These actions were restricted to the inflamed paws (FIG. 7) and were prevented by the $CB_1$ antagonist rimonabant, but not by the $CB_2$ antagonist AM630 (each at 1 mg-kg$^{-1}$, i.p.) (FIG. 4a-c). URB937 did not affect paw edema 4 h after carrageenan injection, but reversed it 24 h after the injection through a mechanism that was sensitive both to $CB_1$ and $CB_2$ receptor blockade (FIG. 4d).

Figure 5A:
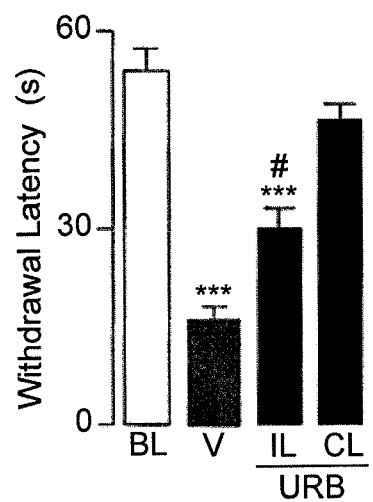
FIG. 5 URB937 suppresses pain behavior elicited by peripheral neural injury in mice. (a-c) Effects of single administration of vehicle (shaded bars) or URB937 (closed bars; 1 mg-kg$^{-1}$, i.p.) on (a) mechanical hyperalgesia, (b) thermal hyperalgesia, and (c) mechanical allodynia induced by sciatic nerve ligation. (d-f) Effects of repeated URB937 injections (1 mg-kg$^{-1}$, i.p, once-daily for 4 consecutive days) on (d) mechanical hyperalgesia, (e) thermal hyperalgesia, and (f) mechanical allodynia. BL, baseline (measured before ligation); IL, ipsilateral (ligated) paw; CL, contralateral (non-ligated) paw. Results are expressed as mean±s.e.m.; n=6. ***$P<0.001$ vs baseline; #$P<0.05$ vs vehicle; ##$P<0.01$ vs vehicle; ###$P<0.001$ vs vehicle.
Figure 5B:
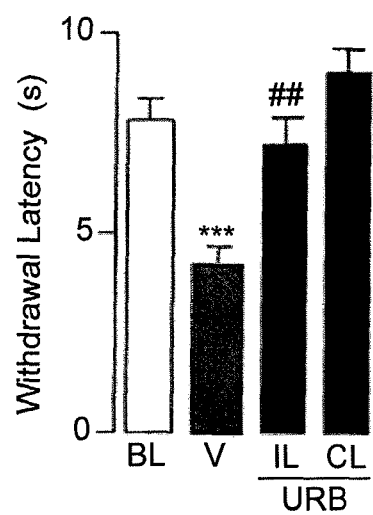
Figure 5C:
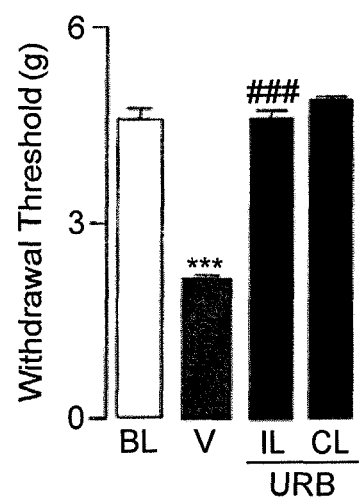
Figure 5D:
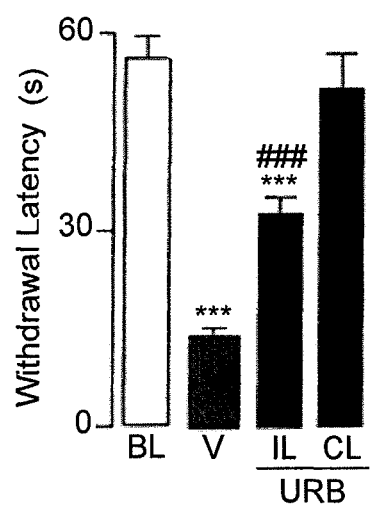
Figure 5E:
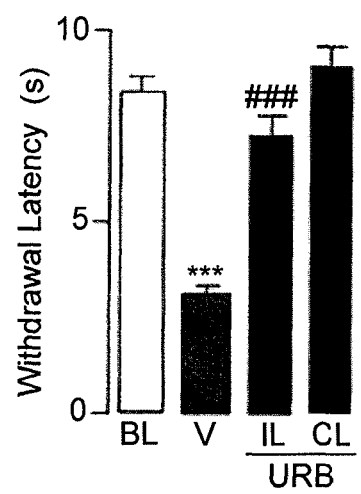
Figure 5F:
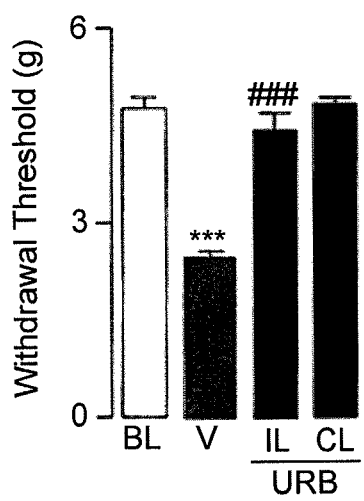

In another group of mice, we produced peripheral nerve damage by loosely tying the left sciatic nerve[24]. A single dose of URB937 (1 mg-kg$^{-1}$, i.p., 2 h before testing), administered one week after surgery, attenuated thermal hyperalgesia and suppressed mechanical hyperalgesia and mechanical allodynia in the operated paws (FIG. 5a-c). Notably, this effect was not accompanied by changes in the reactivity of non-operated paws, indicating that URB937 selectively normalized mechanical and thermal thresholds altered by nerve injury (FIG. 5a-c). Finally, we examined the impact of repeated injections of URB937 (1 mg-kg$^1$, i.p., 2 h before testing) once daily for 4 days, starting 3 days after nerve ligation. The treatment elicited an antinociceptive effect that was undistinguishable from that caused by single drug dosing (FIG. 5d-f), which is suggestive that URB937 alleviates established neuropathic pain without inducing tolerance.

REFERENCES

1 Stein, C., Schafer, M., & Machelska, H., Attacking pain at its source: new perspectives on opioids. Nat Med 9 (8), 1003-1008 (2003).
2 Stein, C. & Zollner, C., Opioids and sensory nerves. Handb Exp Pharmacol (194), 495-518 (2009).
3 Calignano, A., La Rana, G., Giuffrida, A., & Piomelli, D., Control of pain initiation by endogenous cannabinoids. Nature 394 (6690), 277-281 (1998).
4 Jaggar, S. I., Sellaturay, S., & Rice, A. S., The endogenous cannabinoid anandamide, but not the CB2 ligand palmitoylethanolamide, prevents the viscero-visceral hyper-reflexia associated with inflammation of the rat urinary bladder. Neurosci Lett 253 (2), 123-126 (1998).
5 Nackley, A. G., Suplita, R. L., 2nd, & Hohmann, A. G., A peripheral cannabinoid mechanism suppresses spinal fos protein expression and pain behavior in a rat model of inflammation. Neuroscience 117 (3), 659-670 (2003).
6 Dziadulewicz, E. K. et al., Naphthalen-1-yl-(4-pentyloxynaphthalen-1-yl)methanone: a potent, orally bioavailable human CB1/CB2 dual agonist with antihyperalgesic properties and restricted central nervous system penetration. J Med Chem 50 (16), 3851-3856 (2007).
7 Anand, P., Whiteside, G., Fowler, C. J., & Hohmann, A. G., Targeting CB2 receptors and the endocannabinoid system for the treatment of pain. Brain Res Rev 60 (1), 255-266 (2009).
8 Agarwal, N. et al., Cannabinoids mediate analgesia largely via peripheral type 1 cannabinoid receptors in nociceptors. Nat Neurosci 10 (7), 870-879 (2007).
9 Kaufmann, I. et al., Enhanced anandamide plasma levels in patients with complex regional pain syndrome following traumatic injury: a preliminary report. Eur Surg Res 43 (4), 325-329 (2009).
10 Richardson, D. et al., Characterisation of the cannabinoid receptor system in synovial tissue and fluid in patients with osteoarthritis and rheumatoid arthritis. Arthritis Res Ther 10 (2), R43 (2008).
11 Mitrirattanakul, S. et al., Site-specific increases in peripheral cannabinoid receptors and their endogenous ligands in a model of neuropathic pain. Pain 126 (1-3), 102-114 (2006).
12 Schlosburg, J. E., Kinsey, S. G., & Lichtman, A. H., Targeting fatty acid amide hydrolase (FAAH) to treat pain and inflammation. AAPS J 11 (1), 39-44 (2009).
13 Kathuria, S. et al., Modulation of anxiety through blockade of anandamide hydrolysis. Nat Med 9 (1), 76-81 (2003).
14 Piomelli, D. et al., Pharmacological profile of the selective FAAH inhibitor KDS-4103 (URB597). CNS Drug Rev 12 (1), 21-38 (2006).
15 Clapper, J. R. et al., A second generation of carbamate-based fatty acid amide hydrolase inhibitors with improved activity in vivo. ChemMedChem 4 (9), 1505-1513 (2009).
16 Alexander, J. P. & Cravatt, B. F., Mechanism of carbamate inactivation of FAAH: implications for the design of covalent inhibitors and in vivo functional probes for enzymes. Chem Biol 12 (11), 1179-1187 (2005).
17 Loscher, W. & Potschka, H., Blood-brain barrier active efflux transporters: ATP-binding cassette gene family. NeuroRx 2 (1), 86-98 (2005).
18 Cravatt, B. F. et al., Supersensitivity to anandamide and enhanced endogenous cannabinoid signaling in mice lacking fatty acid amide hydrolase. Proc Natl Acad Sci USA 98 (16), 9371-9376 (2001).
19 Starowicz, K., Nigam, S., & Di Marzo, V., Biochemistry and pharmacology of endovanilloids. Pharmacol Ther 114 (1), 13-33 (2007).
20 LoVerme, J., La Rana, G., Russo, R., Calignano, A., & Piomelli, D., The search for the palmitoylethanolamide receptor. Life Sci 77 (14), 1685-1698 (2005).
21 Sagar, D. R., Kendall, D. A., & Chapman, V, Inhibition of fatty acid amide hydrolase produces PPAR-alpha-mediated analgesia in a rat model of inflammatory pain. Br J Pharmacol 155 (8), 1297-1306 (2008).
22 Coderre, T. J. & Melzack, R., The contribution of excitatory amino acids to central sensitization and persistent nociception after formalin-induced tissue injury. J Neurosci 12 (9), 3665-3670 (1992).
23 Puig, S. & Sorkin, L. S., Formalin-evoked activity in identified primary afferent fibers: systemic lidocaine suppresses phase-2 activity. Pain 64 (2), 345-355 (1996).
24 Bennett, G. J. & Xie, Y. K., A peripheral mononeuropathy in rat that produces disorders of pain sensation like those seen in man. Pain 33 (1), 87-107 (1988).
25 Ahluwalia, J., Yaqoob, M., Urban, L., Bevan, S., & Nagy, I., Activation of capsaicin-sensitive primary sensory neurones induces anandamide production and release. J Neurochem 84 (3), 585-591 (2003).
26 Liu, J. et al., A biosynthetic pathway for anandamide. Proc Natl Acad Sci USA 103 (36), 13345-13350 (2006).
27 Hohmann, A. G. & Herkenham, M., Localization of central cannabinoid CB1 receptor messenger RNA in neuronal subpopulations of rat dorsal root ganglia: a double-label in situ hybridization study. Neuroscience 90 (3), 923-931 (1999).
28 Hohmann, A. G. & Herkenham, M., Cannabinoid receptors undergo axonal flow in sensory nerves. Neuroscience 92 (4), 1171-1175 (1999).
29 Richardson, J. D., Kilo, S., & Hargreaves, K. M., Cannabinoids reduce hyperalgesia and inflammation via interaction with peripheral CB1 receptors. Pain 75 (1), 111-119 (1998).
30 Mackie, K., Cannabinoid receptors as therapeutic targets Annu Rev Pharmacol Toxicol 46, 101-122 (2006).
31 LoVerme, J. et al., Rapid broad-spectrum analgesia through activation of peroxisome proliferator-activated receptor-alpha. J Pharmacol Exp Ther 319 (3), 1051-1061 (2006).

32 Guindon, J. & Hohmann, A. G., Cannabinoid CB2 receptors: a therapeutic target for the treatment of inflammatory and neuropathic pain. Br J Pharmacol 153 (2), 319-334 (2008).

33 Cravatt, B. F. et al., Functional disassociation of the central and peripheral fatty acid amide signaling systems. Proc Natl Acad Sci USA 101 (29), 10821-10826 (2004).

34 Lever, I. J. et al., Localization of the endocannabinoid-degrading enzyme fatty acid amide hydrolase in rat dorsal root ganglion cells and its regulation after peripheral nerve injury. J Neurosci 29 (12), 3766-3780 (2009).

35 Tegeder, I. et al., Peripheral opioid analgesia in experimental human pain models. Brain 126 (Pt 5), 1092-1102 (2003).

36 Mor, M. et al., Cyclohexylcarbamic acid 3'- or 4'-substituted biphenyl-3-yl esters as fatty acid amide hydrolase inhibitors: synthesis, quantitative structure-activity relationships, and molecular modeling studies. J Med Chem 47 (21), 4998-5008 (2004).

37 King, A. R. et al., URB602 inhibits monoacylglycerol lipase and selectively blocks 2-arachidonoylglycerol degradation in intact brain slices. Chem Biol 14 (12), 1357-1365 (2007).

38 Astarita, G., Ahmed, F., & Piomelli, D., Identification of biosynthetic precursors for the endocannabinoid anandamide in the rat brain. J Lipid Res 49 (1), 48-57 (2008).

39 Russo, R. et al., The fatty acid amide hydrolase inhibitor URB597 (cyclohexylcarbamic acid 3'-carbamoylbiphenyl-3-yl ester) reduces neuropathic pain after oral administration in mice. J Pharmacol Exp Ther 322 (1), 236-242 (2007).

40 Calignano, A., La Rana, G., & Piomelli, D., Antinociceptive activity of the endogenous fatty acid amide, palmityethanolamide. Eur J Pharmacol 419 (2-3), 191-198 (2001).

41 Tjolsen, A., Berge, O. G., Hunskaar, S., Rosland, J. H., & Hole, K., The formalin test: an evaluation of the method. Pain 51 (1), 5-17 (1992).

42 Fegley, D. et al., Characterization of the fatty acid amide hydrolase inhibitor cyclohexyl carbamic acid 3'-carbamoyl-biphenyl-3-yl ester (URB597): effects on anandamide and oleoylethanolamide deactivation. J Pharmacol Exp Ther 313 (1), 352-358 (2005).

43 Cadas, H., di Tomaso, E., & Piomelli, D., Occurrence and biosynthesis of endogenous cannabinoid precursor, N-arachidonoyl phosphatidylethanolamine, in rat brain. J Neurosci 17 (4), 1226-1242 (1997).

44 Presley, R. W., Menetrey, D., Levine, J. D., & Basbaum, A. I., Systemic morphine suppresses noxious stimulus-evoked Fos protein-like immunoreactivity in the rat spinal cord. J Neurosci 10 (1), 323-335 (1990).

45 Paxinos, G. & Watson, C., The rat brain in stereotaxic coordinates, 6th ed. (Academic Press/Elsevier, Amsterdam; Boston; 2007).

46 Ruda, M. A., Ling, Q. D., Hohmann, A. G., Peng, Y. B., & Tachibana, T., Altered nociceptive neuronal circuits after neonatal peripheral inflammation. Science 289 (5479), 628-631 (2000).

47 Hargreaves, K., Dubner, R., Brown, F., Flores, C., & Joris, J., A new and sensitive method for measuring thermal nociception in cutaneous hyperalgesia. Pain 32 (1), 77-88 (1988).

48. Greenhouse and Geisser, 1959. *Psychometrika*. 24:95-112.

TABLE 1

In vitro and in vivo characterization of O-arylcarbamate FAAH inhibitors

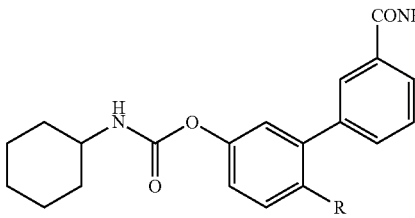

| Compound | R | $IC_{50}$ (nM)[a] | FAAH Inhibition in liver (%)[b] | FAAH Inhibition in brain (%)[b] |
|---|---|---|---|---|
| 1a (URB597) | H | 7.7 ± 1.5 | N.D. | 96.2 ± 0.4 |
| 1b (URB937) | OH | 26.8 ± 4.9 | 91.7 ± 0.7 | −3.0 ± 8.0 |
| 1c | $OCH_3$ | 45.3 ± 14.1 | 94.6 ± 0.7 | 86.4 ± 2.1 |
| 1d | $CH_3$ | 20.5 ± 0.6 | 93.0 ± 1.1 | 91.9 ± 1.5 |
| 1e | F | 49.7 ± 5.8 | 90.7 ± 1.2 | 89.7 ± 1.3 |
| 1f | $NH_2$ | 42.5 ± 4.2 | 92.2 ± 0.6 | 23.2 ± 2.1 |

[a]$IC_{50}$ measured in membrane preparation of rat brain
[b]FAAH inhibition measured ex vivo 1 h after a single injection in mice (1 mg-$kg^{-1}$, i.p.)

TABLE 2

% of FAAH inhibition after URB937 1 mg/Kg i.p. administration

| | Mice | Rat |
|---|---|---|
| Brain | −3.0 ± 8.0 | 0.2 ± 6.7 |
| Colon | 84.7 ± 0.3*** | 90.8 ± 2.0** |
| Duodenum | 84.3 ± 1.4*** | 89.4 ± 0.1*** |
| Hypothalamus | 18.4 ± 13.8 | 10.2 ± 5.8 |
| Illeum | 86.8 ± 2.4*** | 91.5 ± 2.8*** |
| Jejunum | 90.0 ± 1.4*** | 90.3 ± 0.7*** |
| Kidney | 88.3 ± 1.0*** | 91.4 ± 0.5*** |
| Liver | 91.7 ± 0.7*** | 92.1 ± 0.3*** |
| Lungs | N.D. | 93.5 ± 1.8** |
| Spinal cord | 17.7 ± 10.6 | 19.2 ± 15.7 |
| Spleen | 72.5 ± 0.7*** | 86.1 ± 2.1** |

FAAH activity was not detectable (N.D.) in heart, skeletal, muscle, pancreas or skin.
***P < 0.001;
**P < 0.01;
n = 3

What is claimed is:
1. A compound having the formula:

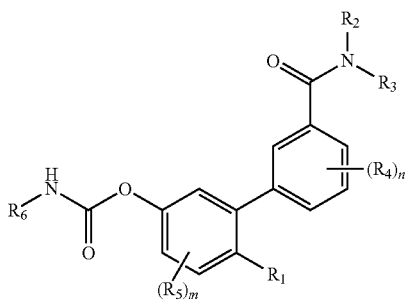

wherein $R_1$ is selected from the group consisting of hydroxy and the physiologically hydrolyzable esters thereof, —OC(O)$R_7$, —O—CO—$NR_8R_9$ and —$NR_8R_9$, wherein $R_7$ is substituted or unsubstituted hydrocarbyl and $R_8$ and $R_9$ are independently selected from the group consisting of hydrogen and substituted or unsubstituted hydrocarbyl;

R$_2$ and R$_3$ are independently selected from the group consisting of hydrogen and substituted or unsubstituted hydrocarbyl;

each R$_4$ is independently selected from the group consisting of halogen and substituted or unsubstituted hydrocarbyl and n is an integer from 0 to 4;

each R$_5$ is independently selected from the group consisting of halo and substituted or unsubstituted hydrocarbyl and m is an integer from 0 to 3;

R$_6$ is substituted or unsubstituted cyclohexyl; and the pharmaceutically acceptable salts thereof.

2. The compound of claim 1, wherein R$_1$ is —OC(O)R$_7$, wherein R$_7$ is substituted or unsubstituted hydrocarbyl.

3. The compound of claim 1, wherein R$_1$ is —O—CO—NR$_8$R$_9$.

4. The compound of claim 1, wherein both of R$_2$ and R$_3$ are independently selected from (C$_1$-C$_3$)alkyl and H.

5. The compound of claim 1, wherein R$_6$ is unsubstituted cyclohexyl.

6. The compound of claim 1, wherein R$_4$ and R$_5$ are each independently selected from halogen and substituted or unsubstituted (C$_1$-C$_3$)alkyl.

7. The compound of claim 1, wherein R$_7$ is substituted or unsubstituted (C$_1$-C$_3$)alkyl.

8. The compound of claim 1, wherein R$_1$ is the physiologically hydrolysable ester.

9. The compound of claim 1, wherein R$_1$ is hydroxy and at least one of R$_2$ and R$_3$ is hydrogen.

10. The compound of claim 1, wherein R$_1$ is hydroxy and both of R$_2$ and R$_3$ are hydrogen.

11. The compound of claim 1 in which m is 0.

12. The compound of claim 1 in which n is 0.

13. The compound of claim 1 wherein the sum of m and n is 1, 2, or 3.

14. The compound of claim 1, wherein the compound has the formula:

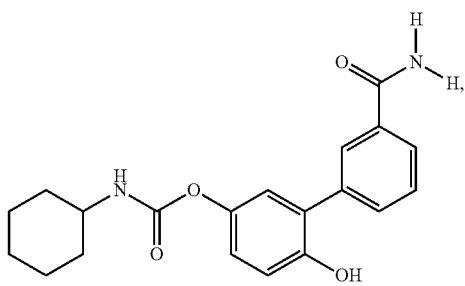

and the pharmaceutically acceptable salts thereof.

15. A pharmaceutical composition comprising a compound of claim 1.

16. A pharmaceutical composition for selectively inhibiting peripheral Fatty Acid Amide Hydrolase (FAAH), said composition comprising a compound of claim 1 and a pharmaceutically acceptable excipient.

17. A method of treating pain by administering to a mammal in need thereof, a therapeutically effective amount of a compound of claim 1, wherein the pains is post trigeminal neuralgia, peripheral or polyneuropathic pain, complex regional pain syndrome, reflex sympathetic dystrophy, diabetic neuropathy, toxic neuropathy, chronic neuropathy caused by chemotherapeutic agents, renal colic pain, liver pain, fibromyalgia, due to compression of a nerve, due to transection of a nerve, due to spinal cord injury, post-surgical pain, or due to scar formation.

18. A method of treating inflammation by administering to a mammal in need thereof a therapeutically effective amount of a compound of claim 1.

19. A method of increasing in a mammal in need thereof peripheral levels of anandamide, oleoylethanolamide (OEA), palmitylethanolamide (PEA), or stearoylethanolamide (SEA) by administering a compound of claim 1.

20. The method of claim 19, wherein the OEA, PEA, SEA or anandamide is endogenous to the mammal.

21. The method of claim 19, wherein the OEA, PEA, SEA or anandamide was administered to the mammal before, after, or contemporaneous with the administration of the compound.

22. The method of claim 19, wherein the administration of the OEA, PEA, SEA or anandamide is contemporaneous with the administration of the compound.

23. The compound of claim 1, wherein R$_2$, R$_3$, R$_7$, R$_8$, and R$_9$ are independently selected from hydrogen and unsubstituted hydrocarbyl.

24. The compound of claim 1, wherein R$_2$, R$_3$, R$_7$, R$_8$, and R$_9$ are independently hydrogen or unsubstituted C$_1$ to C$_3$ hydrocarbyl.

* * * * *